United States Patent
Yu et al.

(10) Patent No.: US 10,808,269 B2
(45) Date of Patent: Oct. 20, 2020

(54) SYNTHESIS OF GLUCAN COMPRISING ALPHA-1,3 GLYCOSIDIC LINKAGES WITH PHOSPHORYLASE ENZYMES

(71) Applicant: DANISCO US INC, Palo Alto, CA (US)

(72) Inventors: Zheyong Yu, Shanghai (CN); Slavko Kralj, Copenhagen (DK); Zhenghong Zhang, Shanghai (CN); Laurie A. Howe, Bear, DE (US)

(73) Assignee: DANISCO US INC CA (US)

( * ) Notice: Subject to any disclaimer, the term of this patent is extended or adjusted under 35 U.S.C. 154(b) by 2 days.

(21) Appl. No.: 16/281,225

(22) Filed: Feb. 21, 2019

(65) Prior Publication Data

US 2019/0264247 A1    Aug. 29, 2019

(30) Foreign Application Priority Data

Feb. 23, 2018   (WO) ............... PCT/CN2018/077004

(51) Int. Cl.
*C12P 19/08* (2006.01)
*C12N 9/10* (2006.01)
*C12P 19/04* (2006.01)
*C12P 19/18* (2006.01)

(52) U.S. Cl.
CPC ............ *C12P 19/08* (2013.01); *C12N 9/1051* (2013.01); *C12P 19/04* (2013.01); *C12P 19/18* (2013.01)

(58) Field of Classification Search
None
See application file for complete search history.

(56) References Cited

PUBLICATIONS

Simpson et al., "Four glucosyltransferases, GtfJ, GtfK, GtfL and GtfM, from *Streptococcus salivarius* ATCC 25975", Microbiology 141: 1451-1460 (1995). (Year: 1995).*

* cited by examiner

*Primary Examiner* — Anand U Desai

(57) ABSTRACT

Reaction compositions are disclosed herein comprising at least water, beta-glucose-1-phosphate (beta-G1P), an acceptor molecule, and an alpha-1,3-glucan phosphorylase enzyme. These reactions can synthesize oligosaccharides and polysaccharides with alpha-1,3 glycosidic linkages. Further disclosed are alpha-1,3-glucan phosphorylase enzymes and methods of use thereof.

20 Claims, No Drawings
Specification includes a Sequence Listing.

ns and methods of using glucan phosphorylase to synthesize such glucan are presently disclosed to address this need.

SYNTHESIS OF GLUCAN COMPRISING ALPHA-1,3 GLYCOSIDIC LINKAGES WITH PHOSPHORYLASE ENZYMES

This application claims the benefit of International Application No. PCT/CN2018/077004 (filed Feb. 23, 2018), which is incorporated herein by reference in its entirety.

FIELD

The present disclosure is in the field of enzymatic reactions. For example, the disclosure pertains to reactions and methods of producing alpha-1,3-glucan using glucan phosphorylase.

REFERENCE TO SEQUENCE LISTING SUBMITTED ELECTRONICALLY

The official copy of the sequence listing is submitted electronically via EFS-Web as an ASCII formatted sequence listing with a file named 20190221_NB41417USNP_SequenceListing.txt created on Feb. 21, 2019, and having a size of about 25 kilobytes and is filed concurrently with the specification. The sequence listing contained in this ASCII-formatted document is part of the specification and is herein incorporated by reference in its entirety.

BACKGROUND

Driven by a desire to use polysaccharides in various applications, researchers have explored for polysaccharides that are biodegradable and that can be made economically from renewably sourced feedstocks. One such polysaccharide is alpha-1,3-glucan, an insoluble glucan polymer characterized by having alpha-1,3-glycosidic linkages. This polymer has been prepared, for example, using a glucosyltransferase enzyme isolated from *Streptococcus salivarius* (Simpson et al., *Microbiology* 141:1451-1460, 1995). Also for example, U.S. Pat. No. 7,000,000 disclosed the preparation of a spun fiber from enzymatically produced alpha-1,3-glucan. Various other glucan materials have also been studied for developing new or enhanced applications. For example, U.S. Patent Appl. Publ. No. 2015/0232819 discloses enzymatic synthesis of several insoluble glucans having mixed alpha-1,3 and -1,6 linkages.

Despite this work, new methods of producing glucan containing alpha-1,3 glycosidic linkages are desired that do not necessarily rely on glucansucrase enzyme activity. Reactions and methods of using glucan phosphorylase to synthesize such glucan are presently disclosed to address this need.

SUMMARY

In one embodiment, the present disclosure concerns a reaction composition comprising at least water, beta-glucose-1-phosphate (beta-G1P), an acceptor molecule, and a phosphorylase enzyme that synthesizes alpha-1,3-glucan.

In another embodiment, the present disclosure concerns a method of producing alpha-1,3-glucan, the method comprising: (a) contacting at least water, beta-glucose-1-phosphate, an acceptor molecule, and a phosphorylase enzyme that synthesizes alpha-1,3-glucan, wherein alpha-1,3-glucan is produced; and (b) optionally, isolating the alpha-1,3-glucan produced in step (a).

BRIEF DESCRIPTION OF THE SEQUENCES

TABLE 1

Summary of Nucleic Acid and Protein SEQ ID Numbers

| Description | Nucleic acid SEQ ID NO. | Protein SEQ ID NO. |
|---|---|---|
| "PspGp3", *Paenibacillus* sp. N027 alpha-1,3-glucan phosphorylase (CRC08506). | 1 | 2 (772 aa) |
| "PspGp3", *Paenibacillus* sp. N027 alpha-1,3-glucan phosphorylase (CRC08506). Nucleotide sequence codon-optimized for expression of SEQ ID NO: 2 in *Bacillus subtilis*. | 3[a] | |
| "ChyGp1", *Caldicellulosiruptor hydrothermalis* alpha-1,3-glucan phosphorylase (CRC08518). | 4 | 5 (765 aa) |
| "ChyGp1", *Caldicellulosiruptor hydrothermalis* alpha-1,3-glucan phosphorylase (CRC08518). Nucleotide sequence codon-optimized for expression of SEQ ID NO: 5 in *B. subtilis*. | 6[a] | |

[a]This DNA coding sequence is codon-optimized for expression in *B. subtilis*, and is merely disclosed as an example of a suitable coding sequence.

DETAILED DESCRIPTION

The disclosures of all cited patent and non-patent literature are incorporated herein by reference in their entirety.

Unless otherwise disclosed, the terms "a" and "an" as used herein are intended to encompass one or more (i.e., at least one) of a referenced feature.

Where present, all ranges are inclusive and combinable, except as otherwise noted. For example, when a range of "1 to 5" (i.e., 1-5) is recited, the recited range should be construed as including ranges "1 to 4", "1 to 3", "1-2", "1-2 & 4-5", "1-3 & 5", and the like.

The term "saccharide" and other like terms herein refer to monosaccharides and/or disaccharides/oligosaccharides, unless otherwise noted. A "disaccharide" herein refers to a carbohydrate having two monosaccharides joined by a glycosidic linkage. An "oligosaccharide" herein can refer to a carbohydrate having 3 to 15 monosaccharides, for example, joined by glycosidic linkages. An oligosaccharide can also be referred to as an "oligomer". Monosaccharides (e.g., glucose and/or fructose) comprised within disaccharides/oligosaccharides can be referred to as "monomeric units", "monosaccharide units", or other like terms.

The terms "alpha-glucan", "alpha-glucan polymer" and the like are used interchangeably herein. An alpha-glucan is a polymer comprising glucose monomeric units linked together by alpha-glycosidic linkages. Alpha-glucan herein can be in the form of an oligosaccharide or polysaccharide.

In typical embodiments, an alpha-glucan herein comprises at least about 80%, 81%, 82%, 83%, 84%, 85%, 86%, 87%, 88%, 89%, 90%, 91%, 92%, 93%, 94%, 95%, 96%, 97%, 98%, 99%, or 100% alpha-glycosidic linkages. Examples of alpha-glucan polymers herein include alpha-1,3-glucan. Glucose as comprised within a saccharide, alpha-glucan, or other carbohydrate herein can be referred to as glucose monomeric unit(s), glucose monomer(s), glucose units, or other like terms.

The terms "poly alpha-1,3-glucan", "alpha-1,3-glucan", "alpha-1,3-glucan polymer" and the like are used interchangeably herein. Alpha-1,3-glucan is a polymer of at least DP3 and comprises glucose monomeric units linked together by glycosidic linkages, wherein at least about 50% of the glycosidic linkages are alpha-1,3. Alpha-1,3-glucan in certain embodiments has about 100% alpha-1,3 glycosidic linkages, or comprises at least about 90% or 95% alpha-1,3 glycosidic linkages. Most or all of the other linkages in alpha-1,3-glucan herein typically are alpha-1,6, though some linkages may also be alpha-1,2 and/or alpha-1,4.

The terms "glycosidic linkage", "glycosidic bond", "linkage" and the like are used interchangeably herein and refer to the covalent bond that joins a carbohydrate (sugar) molecule to another group such as another carbohydrate. The term "alpha-1,3-glycosidic linkage" as used herein refers to the type of covalent bond that joins alpha-D-glucose molecules to each other through carbons 1 and 3 on adjacent alpha-D-glucose rings. The glycosidic linkages of a glucan polymer herein can also be referred to as "glucosidic linkages". Herein, "alpha-D-glucose" is referred to as "glucose", unless otherwise noted.

The glycosidic linkage profile of an alpha-glucan herein can be determined using any method known in the art. For example, a linkage profile can be determined using methods using nuclear magnetic resonance (NMR) spectroscopy (e.g., $^{13}$C NMR or $^{1}$H NMR). These and other methods that can be used are disclosed in, for example, *Food Carbohydrates: Chemistry, Physical Properties, and Applications* (S. W. Cui, Ed., Chapter 3, S. W. Cui, Structural Analysis of Polysaccharides, Taylor & Francis Group LLC, Boca Raton, Fla., 2005), which is incorporated herein by reference.

The "molecular weight" of large alpha-glucan polymers herein can be represented as weight-average molecular weight (Mw) or number-average molecular weight (Mn), the units of which are in Daltons or grams/mole. Alternatively, the molecular weight of large alpha-glucan polymers can be represented as DPw (weight average degree of polymerization) or DPn (number average degree of polymerization). The molecular weight of smaller alpha-glucan polymers such as oligosaccharides typically can be provided as "DP" (degree of polymerization), which simply refers to the number of glucose monomeric units comprised within the alpha-glucan. Various means are known in the art for calculating these various molecular weight measurements such as with high-pressure liquid chromatography (HPLC), size exclusion chromatography (SEC), or gel permeation chromatography (GPC).

Unless otherwise disclosed, the terms "phosphorylase", "phosphorylase enzyme" and the like as used herein refer to a particular class of enzymes belonging to the glycosyl hydrolase 65 (GH65) family according to the CAZy (Carbohydrate-Active EnZymes) database (cazy.org website; see Cantarel et al., 2009, *Nucleic Acids Res.* 37:D233-238, incorporated herein by reference). Such a phosphorylase can reversibly catalyze synthesis (such reversibility is typically only under isolated/in vitro conditions) of a certain type of disaccharide, oligosaccharide, or polysaccharide (e.g., alpha-glucan) and free phosphate (reaction products) from glucose-1-phosphate (G1P) and a suitable acceptor (reaction substrates). An "alpha-1,3-glucan phosphorylase" ("phosphorylase enzyme that synthesizes alpha-1,3-glucan") herein catalyzes synthesis of alpha-1,3 glycosidic linkage-containing oligosaccharides or polysaccharides and free phosphate from beta-G1P and a suitable acceptor. An alpha-1,3-glucan phosphorylase in certain aspects comprises an amino acid sequence that is at least 90% identical to SEQ ID NO:2 or 5. Depending on the acceptor used in an alpha-1,3-glucan phosphorylase reaction herein, an alpha-1,3 glycosidic linkage-containing oligosaccharide or polysaccharide product can (i) be comprised entirely of glucose monomeric units (when acceptor itself is comprised only of one or more glucose units), or (ii) comprise non-glucose monosaccharide units and/or non-saccharide moieties in addition to glucose units (when acceptor itself comprises such other monosaccharide units and/or moieties). Except as otherwise noted herein, either of these product types (i or ii) can optionally be characterized with respect to the alpha-1,3 glycosidic linkage-containing oligosaccharide or polysaccharide that was synthesized from the acceptor (i.e., the product linkage profile does not include the linkages of the acceptor). Such is the case, for example, in describing alpha-1,3-glucan with about 100% alpha-1,3 linkages that was synthesized herein using dextran as an acceptor.

The terms "acceptor", "acceptor molecule", "acceptor compound" and the like are used interchangeably herein. A suitable acceptor herein is contemplated to be an organic molecule comprising at least one hydroxyl moiety (—OH), which hydroxyl moiety is capable of being involved in formation of a glycosidic linkage (involving the oxygen atom of the hydroxyl moiety) with the 1-position of glucose of beta-G1P (phosphate group is replaced during linkage formation) via catalytic activity of an alpha-1,3-glucan phosphorylase herein. A suitable acceptor can be a carbohydrate or non-carbohydrate. Examples of non-carbohydrate acceptors include alcohols, polyols, phenolic compounds, and amino acids. Examples of carbohydrate acceptors include disaccharides, oligosaccharides and polysaccharides; all or some of the monomeric units of a carbohydrate acceptor in some embodiments can be glucose units. The non-reducing end of a carbohydrate acceptor is typically involved in glycosidic linkage formation. The term "initial acceptor" can optionally be used herein to characterize an acceptor as used when preparing an alpha-1,3-glucan phosphorylase reaction. An initial acceptor has not yet had a glucose linked to it by alpha-1,3-glucan phosphorylase. During an alpha-1,3-glucan phosphorylase reaction, an acceptor typically serves iteratively as an acceptor for subsequent glucose addition by the phosphorylase.

"Glucose-1-phosphate" (G1P) as used herein refers to a glucose molecule with a phosphate group on the 1-carbon. G1P herein typically is beta-D-glucose-1-phosphate (beta-G1P), which is D-glucopyranose with beta configuration at the anomeric center. Unless as otherwise disclosed G1P herein is not alpha-D-glucose-1-phosphate (alpha-G1P).

"Inorganic phosphate", which can be denoted as "$P_i$", refers to a free phosphate ion in solution, and is distinguished from phosphate as bound in a phosphate ester such as G1P.

The terms "enzymatic reaction", "enzymatic reaction composition", "glucan phosphorylase reaction", "alpha-1,3-glucan phosphorylase reaction" and like terms are used interchangeably herein and, except as otherwise noted, refer to a reaction that is performed by an alpha-1,3-glucan phosphorylase enzyme. An enzymatic reaction generally refers to an aqueous solution/preparation comprising at least beta-G1P, an acceptor, and an active alpha-1,3-glucan phosphorylase enzyme. It is in such a reaction where the step of contacting water, beta-G1P, acceptor and alpha-1,3-glucan phosphorylase enzyme is performed. The term "under suitable reaction conditions" and like terms refer to reaction conditions that support conversion of substrates (beta-G1P and acceptor) to alpha-1,3-glucan (as extended from the acceptor) and free phosphate products via alpha-1,3-glucan phosphorylase activity. It would be understood that, in certain embodiments, as an alpha-1,3-glucan phosphorylase reaction produces insoluble alpha-1,3-glucan product (i.e., typically alpha-1,3-glucan with a DP of at least 8 or 9), such product is present out of solution (the reaction becomes a mixture).

A "control" enzymatic reaction as used herein refers to a reaction using an alpha-1,3-glucan phosphorylase not comprising an amino acid sequence that is at least 90% identical to SEQ ID NO:2 or 5, for example. All the other features (e.g., substrate concentrations, temperature, pH, time) of a control reaction can be the same as the reaction to which it is being compared.

The term "nigerose" as used herein refers to the disaccharide 3-O-alpha-D-glucopyranosyl-D-glucose.

The terms "dextran", "dextran polymer", "dextran molecule" and the like herein refer to a water-soluble alpha-glucan comprising at least 80% alpha-1,6 glycosidic linkages (with the balance of the linkages typically being all or mostly alpha-1,3).

The term "maltose" as used herein refers to the disaccharide 4-O-alpha-D-glucopyranosyl-D-glucose.

The term "maltose phosphorylase" as used herein refers to an enzyme that catalyzes the reaction of maltose and inorganic phosphate (substrates) to glucose and beta-G1P (products). A maltose phosphorylase is classified under EC 2.4.1.8.

The terms "trehalose", "alpha,alpha-trehalose" and the like herein refer to the disaccharide alpha-D-glucopyranosyl-(1,1)-alpha-D-glucopyranoside.

The term "trehalose phosphorylase" as used herein refers to an enzyme that catalyzes the reaction of trehalose and inorganic phosphate (substrates) to glucose and beta-G1P (products). A trehalose phosphorylase is classified under EC 2.4.1.64.

The term "kojibiose" as used herein refers to the disaccharide 2-alpha-D-glucosyl-D-glucose.

The term "kojibiose phosphorylase" as used herein refers to an enzyme that catalyzes the reaction of kojibiose and inorganic phosphate (substrates) to glucose and beta-G1P (products). A kojibiose phosphorylase is classified under EC 2.4.1.230.

The term "nigerose phosphorylase" as used herein refers to an enzyme that catalyzes the reaction of nigerose and inorganic phosphate (substrates) to glucose and beta-G1P (products). A nigerose phosphorylase is classified under EC 2.4.1.279.

A "second reaction" as used herein refers to a reaction that is in addition to an alpha-1,3-glucan phosphorylase reaction ("first reaction"), and which provides beta-G1P substrate for the first reaction. The combination of at least first and second reactions herein can optionally be referred to as a "coupled reaction". A second reaction herein typically provides beta-G1P by using a phosphorylase and free phosphate to phosphorolyze a disaccharide, oligosaccharide, or polysaccharide, which phosphorolysis produces at least beta-G1P.

The terms "percent by volume", "volume percent", "vol %", "v/v %" and the like are used interchangeably herein.

The percent by volume of a solute in a solution can be determined using the formula: [(volume of solute)/(volume of solution)]×100%.

The terms "percent by weight", "weight percentage (wt %)", "weight-weight percentage (% w/w)" and the like are used interchangeably herein. Percent by weight refers to the percentage of a material on a mass basis as it is comprised in a composition, mixture, or solution.

The terms "aqueous liquid", "aqueous fluid" and the like as used herein can refer to water or an aqueous solution. An "aqueous solution" herein can comprise one or more dissolved salts, where the maximal total salt concentration can be about 3.5 wt % in some embodiments. Although aqueous liquids herein typically comprise water as the only solvent in the liquid, an aqueous liquid can optionally comprise one or more other solvents (e.g., polar organic solvent) that are miscible in water. Thus, an aqueous solution can comprise a solvent having at least about 10 wt % water.

An "aqueous composition" herein has a liquid component that comprises at least about 10 wt % water, for example. Examples of aqueous compositions include mixtures, solutions, dispersions (e.g., colloidal dispersions), suspensions and emulsions, for example. An aqueous composition in certain embodiments can comprise insoluble alpha-glucan as disclosed herein, in which case the aqueous composition can optionally be characterized as a solid-in-liquid composition, given the insolubility of the alpha-glucan.

As used herein, the term "colloidal dispersion" refers to a heterogeneous system having a dispersed phase and a dispersion medium, i.e., microscopically dispersed insoluble particles are suspended throughout another substance (e.g., an aqueous composition such as water or aqueous solution). An example of a colloidal dispersion herein is a hydrocolloid. All, or a portion of, the particles of a colloidal dispersion such as a hydrocolloid can comprise insoluble alpha-glucan of the present disclosure. The terms "dispersant" and "dispersion agent" are used interchangeably herein to refer to a material that promotes the formation and/or stabilization of a dispersion.

A glucan that is "insoluble", "aqueous-insoluble", "water-insoluble" (and like terms) (e.g., insoluble alpha-1,3-glucan) does not dissolve (or does not appreciably dissolve) in water or other aqueous conditions, optionally where the aqueous conditions are further characterized to have a pH of 4-9 (e.g., pH 6-8) and/or temperature of about 1 to 85° C. (e.g., 20-25° C.). In contrast, glucans such as certain oligosaccharides herein that are "soluble", "aqueous-soluble", "water-soluble" and the like (e.g., alpha-1,3-glucan with a DP less than 8) appreciably dissolve under these conditions.

The terms "sequence identity", "identity" and the like as used herein with respect to polynucleotide or polypeptide sequences refer to the nucleic acid residues or amino acid residues in two sequences that are the same when aligned for maximum correspondence over a specified comparison window. Thus, "percentage of sequence identity", "percent identity" and the like refer to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. It would be understood that, when calculating sequence identity between a DNA sequence and an RNA sequence, T residues of the DNA sequence align with, and can be considered "identical" with, U residues of the RNA sequence. For purposes of determining "percent complementarity" of first and second polynucleotides, one can obtain this by determining (i) the percent identity between the first polynucleotide and the complement sequence of the second polynucleotide (or vice versa), for example, and/or (ii) the percentage of bases between the first and second polynucleotides that would create canonical Watson and Crick base pairs.

Percent identity can be readily determined by any known method, including but not limited to those described in: 1) *Computational Molecular Biology* (Lesk, A. M., Ed.) Oxford University: NY (1988); 2) *Biocomputing: Informatics and Genome Projects* (Smith, D. W., Ed.) Academic: NY (1993); 3) *Computer Analysis of Sequence Data, Part I* (Griffin, A. M., and Griffin, H. G., Eds.) Humana: NJ (1994); 4) *Sequence Analysis in Molecular Biology* (von Heinje, G., Ed.) Academic (1987); and 5) *Sequence Analysis Primer* (Gribskov, M. and Devereux, J., Eds.) Stockton: NY (1991), all of which are incorporated herein by reference.

Preferred methods for determining percent identity are designed to give the best match between the sequences tested. Methods of determining identity and similarity are codified in publicly available computer programs, for example. Sequence alignments and percent identity calculations can be performed using the MEGALIGN program of the LASERGENE bioinformatics computing suite (DNASTAR Inc., Madison, Wis.), for example. Multiple alignment of sequences can be performed, for example, using the Clustal method of alignment which encompasses several varieties of the algorithm including the Clustal V method of alignment (described by Higgins and Sharp, *CABIOS.* 5:151-153 (1989); Higgins, D. G. et al., *Comput. Appl. Biosci.*, 8:189-191 (1992)) and found in the MEGALIGN v8.0 program of the LASERGENE bioinformatics computing suite (DNASTAR Inc.). For multiple alignments, the default values can correspond to GAP PENALTY=10 and GAP LENGTH PENALTY=10. Default parameters for pairwise alignments and calculation of percent identity of protein sequences using the Clustal method can be KTUPLE=1, GAP PENALTY=3, WINDOW=5 and DIAGONALS SAVED=5. For nucleic acids, these parameters can be KTUPLE=2, GAP PENALTY=5, WINDOW=4 and DIAGONALS SAVED=4. Additionally, the Clustal W method of alignment can be used (described by Higgins and Sharp, *CABIOS.* 5:151-153 (1989); Higgins, D. G. et al., *Comput. Appl. Biosci.* 8:189-191(1992); Thompson, J. D. et al, *Nucleic Acids Research*, 22 (22): 4673-4680, 1994) and found in the MEGALIGN v8.0 program of the LASERGENE bioinformatics computing suite (DNASTAR Inc.). Default parameters for multiple alignment (protein/nucleic acid) can be: GAP PENALTY=10/15, GAP LENGTH PENALTY=0.2/6.66, Delay Divergen Seqs (%)=30/30, DNA Transition Weight=0.5, Protein Weight Matrix=Gonnet Series, DNA Weight Matrix=IUB.

Various polypeptide amino acid sequences and polynucleotide sequences are disclosed herein as features of certain embodiments. Variants of these sequences that are at least about 70-85%, 85-90%, or 90%-95% identical to the sequences disclosed herein can be used or referenced. Alternatively, a variant amino acid sequence or polynucleotide sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence has the same function/activity of the disclosed sequence, or at least about 80%, 81%, 82%, 83%, 84%, 85%, 86%, 87%, 88%, 89%, 90%, 91%, 92%, 93%, 94%, 95%, 96%, 97%, 98%, or 99% of the function/activity of the disclosed sequence. Any polypeptide amino acid sequence disclosed herein not beginning with a methionine can typically further comprise at least a start-methionine at the N-terminus of the amino acid sequence. In contrast, any polypeptide amino acid sequence disclosed herein beginning with a methionine can optionally lack such a methionine residue.

The term "isolated" as used herein characterizes a substance (or process) in a form or environment that does not occur in nature. A non-limiting example of an isolated substance includes any non-naturally occurring substance such as alpha-1,3-glucan or any other polymer as synthesized herein (as well as the presently disclosed alpha-1,3-glucan phosphorylase reactions and processes used in preparation thereof). It is believed that the embodiments disclosed herein are synthetic/man-made (could not have been made except for human intervention/involvement), and/or have properties that are not naturally occurring.

The term "increased" as used herein can refer to a quantity or activity that is at least about 1%, 2%, 3%, 4%, 5%, 6%, 7%, 8%, 9%, 10%, 11%, 12%, 13%, 14%, 15%, 16%, 17%, 18%, 19%, 20%, 50%, 100%, or 200% more than the quantity or activity for which the increased quantity or activity is being compared. The terms "increased", "elevated", "enhanced", "greater than", "improved" and the like are used interchangeably herein.

New methods of producing glucan containing alpha-1,3 glycosidic linkages are desired that do not necessarily rely on glucansucrase enzyme activity. Reactions and methods of using glucan phosphorylase to synthesize such glucan are presently disclosed to address this need.

Certain embodiments of the present disclosure concern a reaction composition comprising at least water, beta-G1P, a suitable acceptor molecule, and a phosphorylase enzyme that synthesizes alpha-1,3-glucan (i.e., an alpha-1,3-glucan phosphorylase). Significantly, such enzymatic reactions produce alpha-1,3-glucan, thereby representing what is believed to be a new means for producing alpha-1,3-glucan. Such new means are, if desired, completely independent from using a glucansucrase for producing alpha-1,3-glucan.

An enzyme with alpha-1,3-glucan phosphorylase activity suitable for use in an enzymatic reaction as presently disclosed can comprise, or consist of, an amino acid sequence that is 100% identical to, or at least 80%, 81%, 82%, 83%, 84%, 85%, 86%, 87%, 88%, 89%, 90%, 91%, 92%, 93%, 94%, 95%, 96%, 97%, 98%, 99%, or 99.5% identical to, SEQ ID NO:2 or SEQ ID NO:5, for example. In some aspects, an alpha-1,3-glucan phosphorylase enzyme with between 80-99.5% amino acid identity with SEQ ID NO:2 or 5 can have some of (e.g., at least 30%, 40%, 50%, 60%, 70%, 80%, or 90% of), or all of, the enzymatic activity of an alpha-1,3-glucan phosphorylase of SEQ ID NO:2 or 5, respectively.

A polynucleotide sequence herein encoding SEQ ID NO:2 or 5 (or a related amino acid sequence with 90% identity thereto) can optionally comprise a nucleotide sequence that is 100% identical to, or at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to, SEQ ID NO:1 or 4, respectively. Examples of such sequences herein are SEQ ID NOs:3 and 6, respectively.

Given that certain amino acids share similar structural and/or charge features with each other (i.e., conserved), one or more amino acids of an alpha-1,3-glucan phosphorylase sequence herein (and/or other types of polypeptides herein) can optionally be substituted with a conserved amino acid residue ("conservative amino acid substitution") as follows:
1. The following small aliphatic, nonpolar or slightly polar residues can substitute for each other: Ala (A), Ser (S), Thr (T), Pro (P), Gly (G);
2. The following polar, negatively charged residues and their amides can substitute for each other: Asp (D), Asn (N), Glu (E), Gln (Q);
3. The following polar, positively charged residues can substitute for each other: His (H), Arg (R), Lys (K);
4. The following aliphatic, nonpolar residues can substitute for each other: Ala (A), Leu (L), Ile (I), Val (V), Cys (C), Met (M); and
5. The following large aromatic residues can substitute for each other: Phe (F), Tyr (Y), Trp (W).

In some aspects, an enzyme with alpha-1,3-glucan phosphorylase activity herein can be obtained (or is obtainable) from a microbial source, such as a bacteria or fungus (e.g., yeast). Examples of bacteria herein include *Paenibacillus* species and *Caldicellulosiruptor* species. Examples of *Paenibacillus* species herein include *P. barengoltzii, P. rubinfantis, P. alvei, P. azotofixans, P. dendritiformis, P. durum, P. koreensis*, and *P. larvae*. Examples of *Caldicellulosiruptor* species herein include *C. hydrothermalis, C. kronotskyensis, C. acetigenus, C. bescii, C. owensensis, C. saccharolyticus, C. lactoaceticus*, and *C. kristjanssonii*.

Examples of enzymes with alpha-1,3-glucan phosphorylase activity herein can be any of the disclosed alpha-1,3-glucan phosphorylase amino acid sequences and that further include 1-300 (or any integer there between [e.g., 10, 20, 30, 40, 50, 75, 100, 150, 200, 250]) residues on the N-terminus and/or C-terminus. Such additional residues may be a heterologous sequence such as an epitope tag (at either N- or C-terminus) or a heterologous signal peptide (at N-terminus), for example. In those embodiments in which a heterologous amino acid sequence is incorporated at the N-terminus, such a heterologous sequence can be adjacent to the original start-methionine of the alpha-1,3-glucan phosphorylase, or can replace the original start methionine, for example. In the latter embodiment, a new start-methionine can be at the N-terminus of the heterologous sequence.

An enzyme with alpha-1,3-glucan phosphorylase activity as presently disclosed typically lacks an N-terminal signal peptide. However, an expression system for producing an alpha-1,3-glucan phosphorylase enzyme can optionally employ an enzyme-encoding polynucleotide that further comprises sequence encoding an N-terminal signal peptide to direct extra-cellular secretion. The signal peptide in such embodiments is cleaved from the enzyme during the secretion process. Since it is believed that alpha-1,3-glucan phosphorylase enzymes disclosed herein (e.g., SEQ ID NOs:2 and 5) are not associated with a signal peptide, any added signal peptide can be considered as heterologous to the enzyme. An example of a signal peptide herein is one from a bacterial species (e.g., a *Bacillus* species such as *B. subtilis*) or fungal species.

An alpha-1,3-glucan phosphorylase herein can be prepared by fermentation of an appropriately engineered microbial strain, for example. Recombinant enzyme production by fermentation is well known in the art using microbial species such as *E. coli, Bacillus* strains (e.g., *B. subtilis*), *Ralstonia eutropha, Pseudomonas fluorescens, Saccharomyces cerevisiae, Pichia pastoris, Hansenula polymorpha*, and species of *Aspergillus* (e.g., *A. awamori*), *Trichoderma* (e.g., *T. reesei*), and *Myceliophthora* (e.g., *M. thermophila*) (e.g., see Adrio and Demain, *Biomolecules* 4:117-139, 2014, which is incorporated herein by reference). A nucleotide sequence encoding an alpha-1,3-glucan phosphorylase amino acid sequence is typically linked to a heterologous promoter sequence to create an expression cassette for the enzyme, and/or is codon-optimized accordingly. Such an expression cassette may be incorporated in a suitable plasmid or integrated into the microbial host chromosome, using methods well known in the art. The expression cassette may include a transcriptional terminator nucleotide sequence following the amino acid coding sequence. The expression cassette may also include, between the promoter sequence and phosphorylase amino acid coding sequence, a nucleotide sequence encoding a signal peptide (e.g., heterologous signal peptide) that is designed for direct secretion of the alpha-1,3-glucan phosphorylase. At the end of fermentation, cells may be ruptured accordingly (typically when a signal peptide for secretion is not employed) and the phosphorylase can be isolated using methods such as precipitation, filtration, and/or concentration. Alternatively, a lysate or extract comprising a phosphorylase can be used without further isolation. If the alpha-1,3-glucan phosphorylase was secreted (i.e., it is present in the fermentation broth), it can optionally be used as isolated from, or as comprised in, the fermentation broth. The activity of an alpha-1,3-glucan phosphorylase enzyme can be confirmed by biochemical assay, if desired, such as by measuring phosphorus release when placing the enzyme in a reaction herein containing beta-G1P and a suitable acceptor (e.g., under conditions as described in Example 3 below). In some aspects, one unit of alpha-1,3-glucan phosphorylase activity by an enzyme can be defined as the amount of enzyme that releases 1 µmol of inorganic phosphorus per minute in an aqueous reaction comprising about 10 mM beta-G1P, about 5 mM acceptor (e.g., nigerose), and about 50 mM Tris-HCl buffer (about pH 7.0), incubated at about 37° C. for about 10 minutes. Inorganic phosphate release can optionally be gauged using the PiBlue™ Phosphate Assay Kit (BioAssay Systems, Hayward, Calif.). An alpha-1,3-glucan phosphorylase enzyme herein is not believed to have maltose phosphorylase activity, for example. Since an alpha-1,3-glucan phosphorylase enzyme herein produces oligosaccharides/polysaccharides, it would be understood that such an enzyme is not a nigerose phosphorylase.

An alpha-1,3-glucan phosphorylase reaction herein produces alpha-1,3-glucan. In some aspects, at least about 50%, 60%, 70%, 80%, 85%, 90%, 91%, 92%, 93%, 94%, 95%, 96%, 97%, 98%, 99%, or 100% (or any integer between 50% and 100%) of the constituent glycosidic linkages of alpha-1,3-glucan herein are alpha-1,3 linkages. In some aspects, accordingly, alpha-1,3-glucan has less than about 50%, 40%, 30%, 20%, 15%, 10%, 9%, 8%, 7%, 6%, 5%, 4%, 3%, 2%, 1%, or 0% (or any integer value between 0% and 50%) glycosidic linkages that are not alpha-1,3. It should be understood that the higher the percentage of alpha-1,3 linkages present in alpha-1,3-glucan, the greater the probability that the alpha-1,3-glucan is linear, since there are lower occurrences of certain linkages forming branch points in the polymer. Thus, alpha-1,3-glucan with 100% alpha-1,3 linkages is completely linear. In certain embodiments, alpha-1,3-glucan has no branch points or less than about 5%, 4%, 3%, 2%, or 1% branch points as a percent of the glycosidic linkages in the polymer. Except as otherwise noted herein, a given linkage profile characterizes that of the alpha-1,3-glucan as synthesized from an acceptor (i.e., the linkage profile does not include the linkage profile of the acceptor).

Alpha-1,3-glucan herein can have a molecular weight in DP of about, or at least about, 3, 4, 5, 6, 7, 8, 9, 10, 11, 12, 13, 14, 15, 16, 17, 18, 19, 20, 21, 22, 23, 24, 25, 26, 27, 28, 29, 30, 3-15, 3-20, 3-25, 3-30, 5-15, 5-20, 5-25, 5-30, 10-15, 10-20, 10-25, 10-30, 15-20, 15-25, 15-30, 20-25, 20-30, or 25-30, for example. In some aspects, any of the aforementioned DP values (e.g., 8 or greater) can instead be represented in terms of DPw or DPn. Except as otherwise noted herein, a given molecular weight characterizes that of the alpha-1,3-glucan as synthesized from an acceptor (i.e., the molecular weight does not include the molecular weight of the acceptor).

Alpha-1,3-glucan in some aspects is insoluble in aqueous conditions. Such insolubility is in non-caustic aqueous conditions, such as those conditions of an alpha-1,3-glucan phosphorylase reaction herein (see below). In general, the solubility of an alpha-1,3-glucan polymer in aqueous settings herein is related to its linkage profile, molecular weight, and/or degree of branching. For example, alpha-1,3-glucan with ≥95% alpha-1,3 linkages is generally insoluble at a DP of 8 or above in aqueous conditions at 20° C. In general, as molecular weight increases, the percentage of alpha-1,3 linkages required for alpha-1,3-glucan insolubility decreases. In some aspects, alpha-1,3-glucan (e.g., with ≥95% alpha-1,3 linkages and a DP of 7 or less) is soluble in the foregoing aqueous conditions. Non-caustic aqueous conditions (or aqueous conditions herein) can include, for example, water or an aqueous solution with a solvent having about, or at least about, 10, 20, 30, 40, 50, 60, 70, 80, 90, 95, or 100 wt % water, and a pH of 4-9 (e.g., pH 4-8 or 6-8).

Alpha-1,3-glucan herein typically does not comprise alternating 1,3 and 1,6 linkages. Alpha-1,3-glucan herein is typically enzymatically derived in an inert vessel (typically under cell-free conditions) (in vitro), and is not derived from a cell wall (e.g., fungal cell wall). Some embodiments are drawn to alpha-1,3-glucan as produced by, or that are producible by, any of the enzymatic reaction processes/conditions disclosed herein.

A suitable acceptor molecule is used in an alpha-1,3-glucan phosphorylase reaction herein, and can optionally be characterized as an "initial acceptor" since it typically is added when first preparing a reaction.

In some aspects, an acceptor molecule comprises a monosaccharide, disaccharide, or oligosaccharide. Yet in some aspects, an acceptor consists of a monosaccharide, disaccharide, or oligosaccharide (e.g., the saccharide acceptor is not chemically derivatized/substituted). A disaccharide or oligosaccharide acceptor molecule typically comprises one or more glucose monomeric units (e.g., at least about 10%, 20%, 30%, 40%, 50%, 60%, 70%, 80%, 90%, or 95% A of the monomeric units are glucose), or comprises only glucose monomeric units. A disaccharide or oligosaccharide can optionally comprise, typically in addition to one or more glucose monomeric units, one or more non-glucose monomeric units. In some aspects, a disaccharide or oligosaccharide comprises only non-glucose monomeric units. A non-glucose monomeric unit of a disaccharide or oligosaccharide (or a non-glucose monomeric acceptor) can be fructose, arabinose, xylose, or galactose in some aspects. Still, in some aspects a monosaccharide acceptor can be glucose, p-nitrophenyl alpha-D-glucopyranoside, or p-nitrophenyl beta-D-glucopyranoside. In some aspects, an acceptor is not fructose, mannose, or glucosamine. An acceptor can be linear (no branches) or branched, for example.

A disaccharide or oligosaccharide acceptor molecule herein can comprise alpha-glycosidic linkages and/or beta-glycosidic linkages. The linkages of an acceptor can be 100% alpha-glycosidic linkages, or at least about 50%, 60%, 70%, 80%, 90%, or 95% alpha-glycosidic linkages, for example. Alpha- or beta-glycosidic linkages between glucose monomers of a disaccharide or oligosaccharide acceptor can comprise one type of, or more than one type of, the following linkages: 1,1; 1,2; 1,3; 1,4; and/or 1,6. Just to illustrate, the linkages can be all alpha-1,3 glucosidic linkages or all alpha-1,6 glucosidic linkages, or a mix of alpha-1,3 and alpha-1,6 glucosidic linkages.

An oligosaccharide acceptor herein can have, have at least, or have up to, 3, 4, 5, 6, 7, 8, 9, 10, 11, 12, 13, 14, or 15 monomeric units, for example.

Particular examples of disaccharide acceptor molecules herein comprise, or consist of, maltose, isomaltose, cellobiose, nigerose, trehalose, maltulose, sucrose, isomaltulose (Palatinose™), turanose, lactose, kojibiose, sophorose, laminaribiose, or gentiobiose. In some aspects, a disaccharide acceptor molecule herein comprises, or consists of, maltose, nigerose, maltulose, or turanose.

In some aspects, an acceptor molecule comprises a polysaccharide. Yet in some aspects, an acceptor consists of a polysaccharide (e.g., the polysaccharide acceptor is not chemically derivatized/substituted). A polysaccharide acceptor molecule typically comprises one or more glucose monomeric units (e.g., at least about 10%, 20%, 30%, 40%, 50%, 60%, 70%, 80%, 90%, or 95% A of the monomeric units are glucose), or comprises only glucose monomeric units (i.e., glucan). A polysaccharide can optionally comprise, typically in addition to one or more glucose monomeric units, one or more non-glucose monomeric units. A non-glucose monomeric unit of a polysaccharide can be fructose, arabinose, xylose, or galactose in some aspects.

A polysaccharide acceptor molecule herein can comprise alpha-glycosidic linkages and/or beta-glycosidic linkages. The linkages of a polysaccharide acceptor can be 100% alpha-glycosidic linkages (e.g., alpha-glucan), or at least about 50%, 60%, 70%, 80%, 90%, or 95% alpha-glycosidic linkages, for example. Alpha- or beta-glycosidic linkages between glucose monomers of a polysaccharide acceptor can comprise one type of, or more than one type of, the following linkages: 1,1; 1,2; 1,3; 1,4; and/or 1,6. Just to illustrate, the linkages can be all alpha-1,3 glucosidic linkages or all alpha-1,6 glucosidic linkages, or a mix of alpha-1,3 and alpha-1,6 glucosidic linkages.

A polysaccharide acceptor herein can have a DP or DPw of about, or at least about, 16, 17, 18, 19, 20, 21, 22, 23, 24, 25, 26, 27, 28, 29, 30, 35, 40, 45, 50, 75, 100, 150, 200, 250, 300, 400, or 500, for example. This DP/DPw can optionally be expressed as a range between any two of these values. Merely as examples, the DP/DPw can be about 20-50, 20-40, or 20-30.

An example of a polysaccharide acceptor herein can comprise, or consist of, dextran. Such dextran can have any of the above features of a polysaccharide acceptor herein, for example, so long as it is a water-soluble alpha-glucan comprising at least 80% alpha-1,6 glycosidic linkages. The following aspects of a dextran acceptor herein are merely provided for illustration purposes.

A dextran acceptor herein can comprise about 100% alpha-1,6-glucosidic linkages (i.e., completely linear dextran backbone), or about, or at least about, 80%, 85%, 90%, 95%, 96%, 97%, 98%, or 99% alpha-1,6-glucosidic linkages, for example. Such a percent alpha-1,6 linkage profile is that taking account of the total of all linkages in the dextran (combination of main chain and, if present, branch portions). Dextran in some aspects can comprise alpha-1,2- or alpha-1,3-linked branches.

A dextran acceptor herein can have a DP/DPw of about, or at least about, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 75, 100, 150, 200, 250, 300, 400, or 500, for example. This DP/DPw can optionally be expressed as a range between any two of these values. Merely as examples, the DP/DPw can be about 20-50, 20-40, or 20-30. Still, in some aspects, the Mw (weight-average molecular weight) of a dextran herein can be about, or at least about, 1000, 2000, 5000, 10000, 25000, 40000, 50000, 75000, 100000, 125000, 150000, 175000, 200000, 240000, 250000, 500000, 750000, or 1000000 Daltons, or be in a range of about 100000-200000, 125000-175000, 130000-170000, 135000-165000, 140000-160000, or 145000-155000 Daltons, for example. Still, in some aspects, dextran can have an Mw of about, or at least about, 2, 3, 4, 5, 6, 7, 8, 9, 10, 20, 30, 40, 50, 60, 70, 80, 90, 100, 110, 120, 130, 140, 150, or 200 million Daltons, or can be in a range of about 50-200, 50-150, 50-120, 80-200, 80-150, or 80-120 million Daltons. Any dextran Mw herein can optionally be expressed as weight-average degree of polymerization (DPw), which is Mw divided by 162.14.

Dextran in some aspects can be chemically derivatized to have chemical substitutions. Examples of derivatized dextran herein include dextran sulfate, dextran ether, and dextran ester. Derivatized dextran can be made from dextran as presently disclosed, for example.

Dextran in some aspects can be any as disclosed in U.S. Patent Appl. Publ. Nos. 2016/0122445, 2010/0284972, 2017/0218093, 2018/0282385, or 2016/0136199, or International Patent Appl. Publ. Nos. WO2017/079595, WO2015/183714, or WO2017/091533, for example, which are all incorporated herein by reference.

The temperature of an alpha-1,3-glucan phosphorylase reaction herein can be controlled, if desired. In some aspects, the temperature is between about 5° C. to about 50° C. The temperature in some aspects is between about 20° C. to about 42° C. In still some aspects, the temperature is about 20, 21, 22, 23, 24, 25, 26, 27, 28, 29, 30, 31, 32, 33, 34, 35, 36, 37, 38, 39, 40, 41, or 42° C.

The pH of an alpha-1,3-glucan phosphorylase reaction composition in some aspects can be about 4.0-9.0, 4.0-8.5, 4.0-8.0, 5.0-8.0, 6.0-8.0, 5.5-7.5, or 5.5-6.5. In some aspects, the pH can be about 4.0, 4.5, 5.0, 5.5, 6.0, 6.5, 7.0, 7.5, or 8.0. The pH can be adjusted or controlled by the addition or incorporation of a suitable buffer, including but not limited to: phosphate (e.g., sodium phosphate buffer), tris (tris [hydroxymethyl] aminomethane; e.g., Tris-HCl), citrate, or a combination thereof. Buffer concentration in the enzymatic reaction can be from 0 mM to about 100 mM, or about 10, 25, 50, or 75 mM, for example. In some aspects, a buffer comprises, or consists of, tris; in this and some other aspects, a buffer optionally does not comprise phosphate.

The initial concentration of beta-G1P in an alpha-1,3-glucan phosphorylase reaction herein can be about, or at least about, 1 to 100 mM, for example. Also for example, the beta-G1P initial concentration can be about, or at least about, 1, 5, 10, 20, 30, 40, 50, 60, 70, 80, 90, or 100 mM, or about 10-50 mM. The initial concentration of an acceptor in an alpha-1,3-glucan phosphorylase reaction herein can be about 1 to 50 mM, for example. In some aspects, the initial concentration of an acceptor can be about, or at least about, 1, 5, 10, 15, 20, 25, 30, 35, 40, 45, or 50 mM, or about 5-10 mM. Still, in some aspects, the initial concentration of an acceptor can be about, or at least about, 0.05, 0.1, 0.5, 1.0, 2.5, 5, 7.5, or 10 g/L. "Initial concentration" of a substrate such as beta-G1P or acceptor refers to the substrate concentration in an enzymatic reaction just after all the reaction components have been added (at least water, beta-G1P, acceptor, alpha-1,3-glucan phosphorylase).

The amount of an alpha-1,3-glucan phosphorylase enzyme comprised in an enzymatic reaction in some aspects can be about 0.01-60 mg/mL. For example, about, or at least about, 0.01, 0.05, 0.1, 0.5, 1, 5, 8, 10, 20, 30, 40, 50, or 60 mg/mL of enzyme can be employed in a reaction. A reaction herein can comprise one, two, or more alpha-1,3-glucan phosphorylase enzymes, for example. In some aspects, only one or two alpha-1,3-glucan phosphorylase enzymes is/are comprised in a reaction. A reaction composition herein can be, and typically is, cell-free (e.g., no whole cells present).

A reaction composition can be contained within any vessel (e.g., an inert vessel/container) suitable for applying one or more reaction conditions disclosed herein. An inert vessel in some aspects can be of stainless steel, plastic, or glass (or comprise two or more of these components) and be of a size suitable to contain a particular reaction. An inert vessel can optionally be equipped with a stirring device. Any of the foregoing features, for example, can be used to characterize an isolated reaction herein.

Completion of a reaction in some aspects can be determined visually (e.g., no more accumulation of insoluble product), and/or by measuring the remaining amount of substrate(s) (beta-G1P and/or acceptor) in the reaction (e.g., no more decrease in substrate levels over time). A reaction herein can be conducted for about, or at least about, 1, 2, 4, 6, 8, 10, 12, 14, 16, 18, 20, 22, 24, 36, 48, 60, 72, 96, 120, 144, or 168 hours, for example.

Embodiments of the present disclosure also concern a method for producing alpha-1,3-glucan, comprising:

(a) contacting at least water, beta-G1P, an acceptor molecule, and a phosphorylase enzyme that synthesizes alpha-1,3-glucan, wherein alpha-1,3-glucan is produced; and (b) optionally, isolating the alpha-1,3-glucan produced in step (a).

The contacting step in a method herein of producing alpha-1,3-glucan can optionally be characterized as providing an enzymatic reaction as presently disclosed, which comprises at least water, beta-G1P, an acceptor molecule, and an alpha-1,3-glucan phosphorylase enzyme. Thus, any feature of an enzymatic reaction composition herein likewise characterizes an alpha-1,3-glucan production method as presently disclosed.

The contacting step in an alpha-1,3-glucan production method can be performed in any number of ways. For example, a desired amount of beta-G1P and/or acceptor can first be dissolved in water (optionally, other components may also be added at this stage of preparation, such as buffer components), followed by addition of one or more alpha-1, 3-glucan phosphorylase enzymes. The reaction may be kept still, or agitated (e.g., via stirring or orbital shaking), for example.

In some aspects, isolating alpha-1,3-glucan can include at least conducting a step of centrifugation, filtration, fractionation, chromatographic separation, dialysis, evaporation, and/or dilution. Isolation of insoluble alpha-1,3-glucan can include at least conducting a centrifugation or filtration step, for example, and can optionally further comprise washing the centrifuged and/or filtered alpha-1,3-glucan one, two, or more times with water or other aqueous liquid. A wash volume can optionally be at least about 10-100% of the volume of the reaction composition used to produce the alpha-1,3-glucan. Washing can be done by various modes, as desired, such as by displacement or re-slurry washing. Isolation herein can optionally further comprise drying alpha-1,3-glucan, and/or preparing an aqueous composition comprising insoluble alpha-1,3-glucan (e.g., dispersion).

An isolated alpha-1,3-glucan product herein, as provided in a dry form, can comprise no more than 2.0, 1.5, 1.0, 0.5, 0.25, 0.10, 0.05, or 0.01 wt % water, for example. In some aspects, an alpha-1,3-glucan product is provided in an amount of at least 1 gram (e.g., at least 2.5, 5, 10, 25, 50, 100, 250, 500, 750, or 1000 g); such an amount can be a dry amount, for example.

Alpha-1,3-glucan herein that has been isolated (optionally characterized as "purified") can be present in a composition at a wt % (dry weight basis) of at least about 50%, 60%, 70%, 80%, 85%, 90%, 91%, 92%, 93%, 94%, 95%, 96%, 97%, 98%, 98.5%, 99%, 99.5%, 99.8%, or 99.9%. Such isolated alpha-1,3-glucan itself can be used as an ingredient/component in a product/application.

Beta-G1P for performing an alpha-1,3-glucan production method herein can be provided directly via addition of isolated beta-G1P (e.g., beta-G1P obtained from a commercial source), for example. Alternatively, beta-G1P can be supplied by providing at least a second reaction, wherein the products of the second reaction comprise beta-G1P (i.e., the second reaction produces beta-G1P as a product). A "second reaction" refers to a reaction that is in addition to the alpha-1,3-glucan phosphorylase reaction performed in the contacting step (which can optionally be denoted as a "first reaction"), and which provides beta-G1P substrate for the alpha-1,3-glucan phosphorylase reaction. A second reaction can optionally be characterized as employing a "beta-G1P-producing enzyme".

A second reaction for providing beta-G1P in some aspects can be provided in the same vessel in which an alpha-1,3-glucan phosphorylase enzymatic reaction is performed (can optionally be characterized as a "coupled reaction"). Alternatively, a second reaction can be performed outside of (separate from) the vessel in which an alpha-1,3-glucan phosphorylase enzymatic reaction is performed. A second reaction can be performed before and/or continuously with an alpha-1,3-glucan phosphorylase enzymatic reaction, for example. The conditions (e.g., time, temperature, pH) of a second reaction herein can be as disclosed for an alpha-1,3-glucan phosphorylase reaction, for example.

A second reaction for providing beta-G1P in some aspects produces beta-G1P by contacting (i) water, (ii) inorganic phosphate, (iii) a disaccharide, oligosaccharide, or polysaccharide (all of which comprise one or more glucose monomeric units), and (iv) a phosphorylase that phosphorolyzes the disaccharide, oligosaccharide, or polysaccharide. A phosphorylase in this aspect is an example of a beta-G1P-producing enzyme herein. The monomeric units of a disaccharide, oligosaccharide, or polysaccharide substrate in a second reaction can be all glucose, or at least 30%, 40%, 50%, 60%, 70%, 80%, or 90% glucose, for example. The glycosidic linkages between the monomeric units can be alpha- and/or beta-linkages, and can be one type of, or more than one type of, the following linkages: 1,1; 1,2; 1,3; 1,4; and/or 1,6. A disaccharide or trisaccharide is typically employed in a second reaction herein.

Examples of a suitable phosphorylase as a beta-G1P-producing enzyme herein include maltose phosphorylase, trehalose phosphorylase, kojibiose phosphorylase and nigerose phosphorylase. In the presence of at least water and inorganic phosphate, these enzymes, respectively, convert maltose, trehalose, kojibiose and nigerose to the products of beta-G1P and glucose. Any of these enzymes, such as a maltose phosphorylase or trehalose phosphorylase, can be bacterial (e.g., *Bacillus* such as *B. subtilis, Enterococcus*) or fungal in origin, for example. Examples of maltose phosphorylase, trehalose phosphorylase and kojibiose phosphorylase enzymes are described the following references, which are all incorporated herein by reference: U.S. Pat. Nos. 5,807,719, 5,939,308, 5,993,889, 5,843,748, 5,565,341 and 5,965,412; U.S. Patent Appl. Publ. Nos. 2002/068349, 2013/302857 and 2007/154996; and International Patent Appl. Publ. No. WO2005/003343.

In some aspects, the substrate of a beta-G1P-producing phosphorylase in a second reaction does not act as an acceptor of an alpha-1,3-glucan phosphorylase herein, or shows very little acceptor function (e.g., less than 5%, 4%, 3%, 2%, 1%, or 0.5% by weight of the substrate is used by alpha-1,3-glucan phosphorylase as an acceptor). Such aspects present typical conditions for conducting a coupled reaction herein. Alternatively, in some aspects, the substrate of a beta-G1P-producing phosphorylase in a second reaction does act as an acceptor of an alpha-1,3-glucan phosphorylase herein. In such aspects, a second reaction typically is conducted separately from the alpha-1,3-glucan phosphorylase reaction (i.e., is not a coupled reaction); however, a coupled reaction can be conducted, if desired, with the understanding that the beta-G1P-producing phosphorylase and alpha-1,3-glucan phosphorylase compete for the same substrate under such conditions.

Non-limiting examples of compositions and methods disclosed herein include:

1. A reaction composition comprising at least water, beta-glucose-1-phosphate (beta-G1P), an acceptor molecule, and a phosphorylase enzyme that synthesizes alpha-1,3-glucan.
2. The reaction composition of embodiment 1, wherein the alpha-1,3-glucan has at least about 50% alpha-1,3 glycosidic linkages.
3. The reaction composition of embodiment 1 or 2, wherein the alpha-1,3-glucan has at least about 90% alpha-1,3 glycosidic linkages.
4. The reaction composition of embodiment 1, 2, or 3, wherein the degree of polymerization (DP) of the alpha-1,3-glucan is at least 3.
5. The reaction composition of embodiment 4, wherein the DP of the alpha-1,3-glucan is at least about 10.
6. The reaction composition of embodiment 1, 2, 3, 4, or 5, wherein the acceptor molecule comprises a disaccharide or oligosaccharide.
7. The reaction composition of embodiment 1, 2, 3, 4, 5, or 6, wherein the acceptor molecule comprises nigerose.
8. The reaction composition of embodiment 1, 2, 3, 4, or 5, wherein the acceptor molecule comprises a polysaccharide.
9. The reaction composition of embodiment 1, 2, 3, 4, 5, or 8, wherein the polysaccharide comprises alpha-glucan.
10. The reaction composition of embodiment 1, 2, 3, 4, 5, 8, or 9, wherein the alpha-glucan comprises dextran.
11. The reaction composition of embodiment 1, 2, 3, 4, 5, 6, 7, 8, 9, or 10, wherein the phosphorylase enzyme comprises an amino acid sequence that is at least 90% identical to SEQ ID NO:2 or SEQ ID NO:5.
12. A method for producing alpha-1,3-glucan, the method comprising: (a) contacting at least water, beta-glucose-1-phosphate (beta-G1P), an acceptor molecule, and a phosphorylase enzyme that synthesizes alpha-1,3-glucan, wherein alpha-1,3-glucan is produced; and (b) optionally, isolating the alpha-1,3-glucan produced in step (a).

13. The method of embodiment 12, wherein the alpha-1,3-glucan phosphorylase enzyme comprises an amino acid sequence that is at least 90% identical to SEQ ID NO:2 or SEQ ID NO:5.

14. The method of embodiment 12 or 13, wherein said beta-G1P is provided in step (a) by providing a second reaction, wherein the products of the second reaction comprise beta-G1P.

15. The method of embodiment 14, wherein the second reaction is provided in the same vessel in which step (a) is performed, and wherein the second reaction is performed before and/or continuously with step (a).

16. The method of embodiment 14 or 15, wherein the second reaction produces beta-G1P by contacting, with each other, (i) water, (ii) inorganic phosphate, (iii) a glucose-comprising disaccharide, oligosaccharide, or polysaccharide, and (iv) a phosphorylase that phosphorolyzes the disaccharide, oligosaccharide, or polysaccharide.

17. The method of embodiment 16, wherein the second reaction comprises: (i) water, inorganic phosphate, maltose, and a maltose phosphorylase, or (ii) water, inorganic phosphate, trehalose, and a trehalose phosphorylase.

EXAMPLES

The present disclosure is further exemplified in the following Examples. It should be understood that these Examples, while indicating certain aspects herein, are given by way of illustration only. From the above discussion and these Examples, one skilled in the art can ascertain the essential characteristics of the disclosed embodiments, and without departing from the spirit and scope thereof, can make various changes and modifications to adapt the disclosed embodiments to various uses and conditions.

Example 1

Cloning and Expression of a Putative *Paenibacillus* Alpha-1,3-Glucan Phosphorylase This Example describes cloning and expression of a putative *Paenibacillus* alpha-1,3-glucan phosphorylase enzyme.

A putative alpha-1,3-glucan phosphorylase, PspGp3, was identified from *Paenibacillus* sp. N027. The nucleic acid sequence encoding PspGp3 was obtained using genomic sequence, and is presented as SEQ ID NO:1. The amino acid sequence of PspGp3 encoded by SEQ ID NO:1 is presented as SEQ ID NO:2.

An alignment of PspGp3 (SEQ ID NO:2) against the GENBANK database via a BLAST search on the National Center for Biotechnology Information (NCBI) website provided the amino acid sequences listed in Table 2.

TABLE 2

| Sequences Provided by BLAST Alignment of PspGp3 (SEQ ID NO: 2) Against the GENBANK Database | | |
|---|---|---|
| GENBANK Accession No. | Percent Identity[a] with PspGp3 | Structural Annotations Provided in Accession No. Entry |
| WP_036646618.1 | 99% | "glycoside hydrolase" (1-772)[b]<br>"maltose phosphorylase; Provisional" (7-759)<br>"Glycosyl hydrolase family 65, N-terminal domain; pfam03636" (25-261)<br>"Glycosyl hydrolase family 65 central catalytic domain; pfam03632" (324-703)<br>"Glycosyl hydrolase family 65, C-terminal domain; pfam03633" (707-755) |
| EES71145.1 | 99% | "glycosyl hydrolase family 65 central catalytic domain protein" (1-788)<br>"maltose phosphorylase; Provisional" (23-775)<br>"Glycosyl hydrolase family 65, N-terminal domain; pfam03636" (41-277)<br>"Glycosyl hydrolase family 65 central catalytic domain; pfam03632" (340-719)<br>"Glycosyl hydrolase family 65, C-terminal domain; pfam03633" (723-771) |
| WP_085170614.1 | 95% | "family 65 glycosyl hydrolase" (1-772)<br>"Glycosyl hydrolase family 65 central catalytic domain; cl27850" (7-759) |
| WP_028539421.1 | 95% | "glycoside hydrolase" (1-772)<br>"maltose phosphorylase; Provisional" (7-759)<br>"Glycosyl hydrolase family 65, N-terminal domain; pfam03636" (25-261)<br>"Glycosyl hydrolase family 65 central catalytic domain; pfam03632" (324-703)<br>"Glycosyl hydrolase family 65, C-terminal domain; pfam03633" (707-755) |
| WP_085278672.1 | 95% | "family 65 glycosyl hydrolase" (1-772)<br>"Glycosyl hydrolase family 65 central catalytic domain; cl27850" (7-759) |
| WP_016313527.1 | 95% | "family 65 glycosyl hydrolase" (1-772)<br>"maltose phosphorylase; Provisional" (7-759)<br>"Glycosyl hydrolase family 65, N-terminal domain; pfam03636" (25-261)<br>"Glycosyl hydrolase family 65 central catalytic domain; pfam03632" (324-703)<br>"Glycosyl hydrolase family 65, C-terminal domain; pfam03633" (707-755) |

TABLE 2-continued

Sequences Provided by BLAST Alignment of PspGp3 (SEQ ID NO: 2) Against the GENBANK Database

| GENBANK Accession No. | Percent Identity[a] with PspGp3 | Structural Annotations Provided in Accession No. Entry |
|---|---|---|
| WP_059042646.1 | 90% | "glycoside hydrolase" (1-768)<br>"maltose phosphorylase; Provisional" (7-753)<br>"Glycosyl hydrolase family 65, N-terminal domain; pfam03636" (25-257)<br>"Glycosyl hydrolase family 65 central catalytic domain; pfam03632" (320-699)<br>"Glycosyl hydrolase family 65, C-terminal domain; pfam03633" (703-752) |
| WP_068782755.1 | 88% | "glycoside hydrolase" (1-772) |
| WP_036626146.1 | 83% | "glycoside hydrolase" (1-768)<br>"maltose phosphorylase; Provisional" (7-750)<br>"Glycosyl hydrolase family 65, N-terminal domain; pfam03636" (25-254)<br>"Glycosyl hydrolase family 65 central catalytic domain; pfam03632" (320-699)<br>"Glycosyl hydrolase family 65, C-terminal domain; pfam03633" (703-750) |
| OMG50072.1 | 82% | "family 65 glycosyl hydrolase" (1-768) |
| WP_059049729.1 | 82% | "glycoside hydrolase" (1-767)<br>"maltose phosphorylase; Provisional" (7-761)<br>"Glycosyl hydrolase family 65, N-terminal domain; pfam03636" (24-257)<br>"Glycosyl hydrolase family 65 central catalytic domain; pfam03632" (320-699)<br>"Glycosyl hydrolase family 65, C-terminal domain; pfam03633" (703-749) |
| WP_018753474.1 | 82% | "glycoside hydrolase" (1-767)<br>"maltose phosphorylase; Provisional" (7-748)<br>"Glycosyl hydrolase family 65, N-terminal domain; pfam03636" (24-257)<br>"Glycosyl hydrolase family 65 central catalytic domain; pfam03632" (320-699)<br>"Glycosyl hydrolase family 65, C-terminal domain; pfam03633" (703-749) |

[a]Query (SEQ ID NO: 2) coverage with listed sequences was about 99% or higher. Amino acid sequences with at least 80% identity to query (or portion thereof) are listed.
[b]Amino acid residues listed parenthetically in table are of respective GENBANK amino acid sequence.

A nucleic acid sequence encoding PspGp3 (SEQ ID NO:2) was optimized for expression in *Bacillus subtilis*, and is presented herein as SEQ ID NO:3. This sequence was synthesized by Generay Biotech Co. (Shanghai, China) and inserted into plasmid p3JM, which is a derivative of plasmid p2JM103BBI (Vogtentanz et al., 2007, *Protein Expr. Purif.* 55:40-52, incorporated herein by reference), resulting in plasmid p3JM-PspGP3 (6699 base pairs). This plasmid construct comprises, inter alia, chloramphenicol-resistance and ampicillin-resistance selection markers, and SEQ ID NO:3 placed downstream of an aprE promoter.

Plasmid p3JM-PspGP3 was used to transform *B. subtilis* cells. Transformed cells were spread onto Luria Agar plates supplemented with 5 ppm chloramphenicol. A correctly transformed colony, which was confirmed by PCR and sequencing, was selected and subjected to fermentation for expression of PspGp3. This expressed PspGp3 product (SEQ ID NO:2), which was recovered from the culture medium, was then analyzed for alpha-1,3-glucan phosphorylase activity, as described in Example 3 below.

Example 2

Cloning and Expression of a Putative *Caldicellulosiruptor* Alpha-1,3-Glucan Phosphorylase This Example describes cloning and expression of a putative *Caldicellulosiruptor* alpha-1,3-glucan phosphorylase enzyme.

A putative alpha-1,3-glucan phosphorylase, ChyGp1, was identified from *Caldicellulosiruptor hydrothermalis*. The nucleic acid sequence encoding ChyGp1 was obtained using genomic sequence, and is presented as SEQ ID N0:4. The amino acid sequence of ChyGp1 encoded by SEQ ID NO:4 is presented as SEQ ID NO:5.

An alignment of ChyGp1 (SEQ ID NO:5) against the GENBANK database via a BLAST search on the NCBI website provided the amino acid sequences listed in Table 3.

TABLE 3

Sequences Provided by BLAST Alignment of ChyGp1 (SEQ ID NO: 5) Against the GENBANK Database

| GENBANK Accession No. | Percent Identity[a] with ChyGp1 | Structural Annotations Provided in Accession No. Entry |
|---|---|---|
| WP_013402045.1 | 100% | "glycoside hydrolase family 65" (1-765)[b] <br> "maltose phosphorylase; Provisional" (8-754) <br> "Glycosyl hydrolase family 65, N-terminal domain; pfam03636" (26-243) <br> "Glycosyl hydrolase family 65 central catalytic domain; pfam03632" (318-694) <br> "Glycosyl hydrolase family 65, C-terminal domain; pfam03633" (702-751) |
| WP_029228899.1 | 96% | "glycoside hydrolase family 65" (1-765) <br> "maltose phosphorylase; Provisional" (8-754) <br> "Glycosyl hydrolase family 65, N-terminal domain; pfam03636" (26-235) <br> "Glycosyl hydrolase family 65 central catalytic domain; pfam03632" (318-694) <br> "Glycosyl hydrolase family 65, C-terminal domain; pfam03633" (702-751) |
| WP_013429160.1 | 95% | "glycoside hydrolase family 65" (1-765) <br> "maltose phosphorylase; Provisional" (8-754) <br> "Glycosyl hydrolase family 65, N-terminal domain; pfam03636" (26-258) <br> "Glycosyl hydrolase family 65 central catalytic domain; pfam03632" (318-694) <br> "Glycosyl hydrolase family 65, C-terminal domain; pfam03633" (702-751) |

[a]Query (SEQ ID NO: 5) coverage with listed sequences was about 100%. Amino acid sequences with at least 80% identity to query are listed.
[b]Amino acid residues listed parenthetically in table are of respective GENBANK amino acid sequence.

A nucleic acid sequence encoding ChyGp1 (SEQ ID NO:5) was optimized for expression in B. subtilis, and is presented herein as SEQ ID NO:6. This sequence was synthesized by Generay Biotech Co. and inserted into plasmid p3JM (Example 1), resulting in plasmid p3JM-ChyGp1 (6678 base pairs). This plasmid construct comprises, inter alia, chloramphenicol-resistance and ampicillin-resistance selection markers, and SEQ ID NO:6 placed downstream of an aprE promoter.

Plasmid p3JM-ChyGp1 was used to transform B. subtilis cells. Transformed cells were spread onto Luria Agar plates supplemented with 5 ppm chloramphenicol. A correctly transformed colony, which was confirmed by PCR and sequencing, was selected and subjected to fermentation for expression of ChyGp1. This expressed ChyGp1 product (SEQ ID NO:5), which was recovered from the culture medium, was then analyzed for alpha-1,3-glucan phosphorylase activity, as described in Example 3 below.

Example 3

Analysis of Phosphorylase Activity of PspGp3 and ChyGp1, and Synthesis of Glucan Thereby This Example describes measuring the phosphorylase activity of the putative alpha-1,3-glucan phosphorylases expressed in Examples 1 and 2 (PspGp3 and ChyGp1, respectively). It was found that these phosphorylases likely synthesize alpha-1,3-glucan, and thus are contemplated to be alpha-1,3-glucan phosphorylases.

Based on Tables 2 and 3, respectively, PspGp3 (SEQ ID NO:2) and ChyGp1 (SEQ ID NO:5) appear to be phosphorylases belonging to the glycosyl hydrolase 65 family (GH65; see Carbohydrate-Active EnZymes [CAZy] database [cazy.org website]; see Cantarel et al., 2009, Nucleic Acids Res. 37:D233-238, incorporated herein by reference). In particular, Tables 2 and 3 suggest that these phosphorylases are maltose phosphorylases.

The activity of each of PspGp3 (SEQ ID NO:2) and ChyGp1 (SEQ ID NO:5) was measured using 10 mM beta-G1P (beta-D-glucose-1-phosphate disodium salt, Tokyo Chemical Industry Co., Ltd., product no. G0339) and 5 mM nigerose (Sigma-Aldrich, product no. 08602) as the initial acceptor. Each assay was performed in water with 50 mM Tris-HCl buffer, pH 7.0, at 37° C. for 10 minutes. Phosphorus release from each enzyme reaction was quantified using PiBlue™ reagent (BioAssay Systems, Hayward, Calif.). One unit of phosphorylase activity was defined as the amount of enzyme that releases 1 µmol of inorganic phosphorus per minute under the above test conditions.

PspGp3 (SEQ ID NO:2) and ChyGp1 (SEQ ID NO:5) (each at 8 mg/L) were individually incubated with 10 mM beta-G1P and 5 mM nigerose for 2 hours in 100-µL reactions with the above pH and temperature conditions. Products from each reaction were analyzed for degree of polymerization (DP) using a high-performance liquid chromatography (HPLC) apparatus equipped with an Aminex® HPX-42A column (eluent: $H_2O$, flow rate: 0.6 mL/min, temperature: 85° C.; detection: RI). The products of each reaction using PspGp3 (SEQ ID NO:2) or ChyGp1 (SEQ ID NO:5) comprised glucan oligosaccharides of DP3, DP4 and DP5 in size. These products are contemplated to have alpha-1,3-glycosidic linkages, based on the observations described in Example 4 below in which PspGp3 (SEQ ID NO:2) and ChyGp1 (SEQ ID NO:5) were each shown to synthesize insoluble products (off a dextran acceptor). Another set of reactions was performed overnight under the above conditions. Each overnight reaction produced glucan oligosaccharides of DP3 to DP10+, with products of DP6 and DP7 predominating. While the oligosaccharide products in this Example may have mostly been soluble (it is possible that some insoluble products were made that were undetectable to the naked eye, since relatively small amounts of substrates were used in the reactions), it is contemplated that appreciable amounts of insoluble products (such as alpha-1,3-linked glucan of DP8, DP9, or higher DP) can be produced in reactions with longer incubation periods (e.g., or 24 hours) and/or higher amounts of substrates (namely beta-G1P). These results are striking in view of Tables 2 and 3; the annotation information in these tables suggests that PspGp3 (SEQ ID NO:2) and ChyGp1 (SEQ ID NO:5) are maltose phosphorylases, which are enzymes that are typically known to convert maltose into glucose and beta-G1P. These results are also notable since alpha-1,3-glucan phosphorylases have never apparently been previously recognized; such enzyme activity is absent from the CAZy online database for GH65 phosphorylases (www.cazy.org/GH65). The present data indicate that PspGp3 (SEQ ID NO:2) and ChyGp1 (SEQ ID NO:5) likely have alpha-1,3-glucan phosphorylase activity.

Example 4

Further Analysis of Glucan Production by PspGp3 and ChyGp1 Phosphorylases

This Example describes likely production of insoluble alpha-1,3-glucan using PspGp3 and ChyGp1 phosphorylases with dextran as an initial acceptor molecule. These results are further to those described in Example 3 above, which shows that PspGp3 and ChyGp1 likely can synthesize alpha-1,3-glucan using nigerose as an initial acceptor molecule.

PspGp3 (SEQ ID NO:2) and ChyGp1 (SEQ ID NO:5) (each at 20 mg/L) were individually provided in 100-µL reactions comprising water, 20 mM beta-G1P and 1 g/L dextran (dextran sulfate sodium salt with relative formula mass of ~4000, Sigma-Aldrich, product no. 75027). Each reaction was performed in 50 mM Tris-HCl buffer, pH 7.0, at 37° C. for 20 hours. HPLC and NMR (nuclear magnetic resonance) analyses were used to determine product molecular weight and linkage profile, respectively. Each reaction was found to produce insoluble glucan, apparently with alpha-1,3 linkages and a DP of about 20. Thus, PspGp3 (SEQ ID NO:2) and ChyGp1 (SEQ ID NO:5) are contemplated to be alpha-1,3-glucan phosphorylases. These results are striking for the same reasons as described in Example 3, namely since PspGp3 (SEQ ID NO:2) and ChyGp1 (SEQ ID NO:5) were suggested to be maltose phosphorylases (see Tables 2 and 3, respectively), and there was apparently no previous recognition of this type of phosphorylase. These results are further striking since twenty-eight other proteins belonging to the GH65 enzyme family were analyzed in this study (data not shown), and only PspGp3 (SEQ ID NO:2) and ChyGp1 (SEQ ID NO:5) produced insoluble product in the above conditions. About ten of these other studied proteins had more than 50% sequence identity to either PspGp3 or ChyGp1.

Thus, it is contemplated that insoluble alpha-1,3-glucan can be synthesized in a reaction comprising at least water, beta-G1P, a suitable acceptor molecule such as dextran, and a glucan phosphorylase such as PspGp3 (SEQ ID NO:2) or ChyGp1 (SEQ ID NO:5).

Example 5

Glucan Production by PspGp3 Phosphorylase in a Coupled Reaction

A reaction with PspGp3 phosphorylase (SEQ ID NO:2) was performed that was similar to the above reaction with this enzyme in Example 4, but in which beta-G1P was provided by way of the activity of maltose phosphorylase on maltose (maltose phosphorylase converts maltose to glucose and beta-G1P). This coupled reaction was set up with water, 50 mM sodium phosphate buffer (pH 7.0), a B. subtilis maltose phosphorylase (0.03 mg/mL), an Enterococcus sp. maltose phosphorylase (0.1 mg/mL, Sigma-Aldrich, product no. M8284), 0.0625 mg/mL PspGp3 (SEQ ID NO:2), 500 mM maltose and 1 g/L dextran (as initial acceptor; T1 dextran [~1000 MW]). The coupled reaction was performed at 37° C. for about sixteen days.

To characterize saccharide products of the coupled reaction, 2-µL samples were taken therefrom and applied accordingly to thin-layer chromatography (TLC) plates (SILICA GEL 60 F254, Merck KGaA, Germany). After drying, the TLC plates were run overnight using 1-butanol:ethanol:water (5:5:3) as the mobile phase. The plates were then air-dried, sprayed with a developing solution (MeOH:$H_2O$:$H_2SO_4$, 45:45:10), and developed at 110° C. for approximately 15 minutes. This analysis showed that saccharides with a DP greater than 7 were synthesized in this coupled reaction.

Separately, products from the coupled reaction were purified (addition of two volumes of ice-cold 96% ethanol followed by spinning for 5 minutes at 5500×g and mixing material in 2 mL water, followed again by a second ethanol wash) and entered into NMR analysis for linkage analysis. It was noted that the average product DP following the first ethanol wash was about 8, while the product DP following the second ethanol wash was about 12 (shorter [soluble] products likely did not precipitate very well, leaving mostly the insoluble ~DP12 product). The NMR results confirmed that the major linkage of the insoluble product (as extended from the dextran acceptor) was alpha-1,3. This result indicates that the insoluble product of PspGp3 phosphorylase (SEQ ID NO:2) as produced in Example 4 above likely also comprised alpha-1,3 linkages.

Thus, alpha-1,3-glucan can be synthesized in a coupled reaction comprising at least water, a suitable acceptor molecule such as dextran, PspGp3 phosphorylase (SEQ ID NO:2), maltose and maltose phosphorylase. In this reaction, the maltose phosphorylase acted on maltose to produce beta-G1P, which in turn was used as substrate (along with dextran) by PspGp3 phosphorylase (SEQ ID NO:2) to produce alpha-1,3-glucan. Other enzymes for producing beta-G1P in a coupled reaction can likely be used instead of maltose phosphorylase, if desired. For example, trehalose phosphorylase and its substrate, trehalose, could be used for beta-G1P production.

The above coupled reaction produced a relatively low amount of insoluble alpha-1,3-glucan product. To investigate this observation further, a panel of different acceptors, including maltose and trehalose, was tested with PspGp3 phosphorylase (SEQ ID NO:2), as well as with ChyGp1 phosphorylase (SEQ ID NO:5). It was observed that maltose was a good acceptor for both enzymes, whereas trehalose was a poor acceptor. Thus, in the above coupled reaction, maltose was likely being used competitively as a substrate by both the maltose phosphorylase (producing beta-G1P) and PspGp3 phosphorylase (SEQ ID NO:2) (as an acceptor for alpha-1,3-glucan synthesis, alongside the use of dextran acceptor). This competitive use of maltose in the coupled reaction likely resulted in the low amount of alpha-1,3-glucan produced. Since trehalose was found to be a poor acceptor for both PspGp3 (SEQ ID NO:2) and ChyGp1 (SEQ ID NO:5) phosphorylases, it is contemplated that use of trehalose and trehalose phosphorylase for beta-G1P production in a coupled reaction herein may allow for better alpha-1,3-glucan synthesis.

What is claimed is:

1. A reaction composition comprising at least water, beta-glucose-1-phosphate (beta-G1P), an acceptor molecule, and a phosphorylase enzyme that synthesizes alpha-1,3-glucan, wherein the phosphorylase enzyme comprises an amino acid sequence that is at least 90% identical to SEQ ID NO:2 or SEQ ID NO:5.

2. The reaction composition of claim 1, wherein the alpha-1,3-glucan has at least about 50% alpha-1,3 glycosidic linkages.

3. The reaction composition of claim 1, wherein the alpha-1,3-glucan has at least about 90% alpha-1,3 glycosidic linkages.

4. The reaction composition of claim 1, wherein the degree of polymerization (DP) of the alpha-1,3-glucan is at least 3.

5. The reaction composition of claim 4, wherein the DP of the alpha-1,3-glucan is at least about 10.

6. The reaction composition of claim 1, wherein the acceptor molecule comprises a disaccharide or oligosaccharide.

7. The reaction composition of claim 6, wherein the acceptor molecule comprises nigerose.

8. The reaction composition of claim 1, wherein the acceptor molecule comprises a polysaccharide.

9. The reaction composition of claim 8, wherein the polysaccharide comprises alpha-glucan.

10. The reaction composition of claim 9, wherein the alpha-glucan comprises dextran.

11. The reaction composition of claim 1, wherein the phosphorylase enzyme comprises an amino acid sequence that is at least 95% identical to SEQ ID NO:2 or SEQ ID NO:5.

12. A method for producing alpha-1,3-glucan, said method comprising:

contacting at least water, beta-glucose-1-phosphate (beta-G1P), an acceptor molecule, and a phosphorylase enzyme that synthesizes alpha-1,3-glucan, wherein the phosphorylase enzyme comprises an amino acid sequence that is at least 90% identical to SEQ ID NO:2 or SEQ ID NO:5, and wherein alpha-1,3-glucan is produced.

13. The method of claim 12, wherein the phosphorylase enzyme comprises an amino acid sequence that is at least 95% identical to SEQ ID NO:2 or SEQ ID NO:5.

14. The method of claim 12, wherein said beta-G1P is provided in step (a) by providing a second reaction, wherein the products of the second reaction comprise beta-G1P.

15. The method of claim 14, wherein the second reaction is provided in the same vessel in which step (a) is performed, and wherein the second reaction is performed before and/or continuously with step (a).

16. The method of claim 14, wherein the second reaction produces beta-G1P by contacting (i) water, (ii) inorganic phosphate, (iii) a glucose-comprising disaccharide, oligosaccharide, or polysaccharide, and (iv) a phosphorylase that phosphorolyzes the disaccharide, oligosaccharide, or polysaccharide.

17. The method of claim 16, wherein the second reaction comprises:
  (i) water, inorganic phosphate, maltose, and a maltose phosphorylase, or
  (ii) water, inorganic phosphate, trehalose, and a trehalose phosphorylase.

18. The method of claim 12, further comprising isolating the alpha-1,3-glucan.

19. The method of claim 12, wherein the alpha-1,3-glucan has at least about 50% alpha-1,3 glycosidic linkages.

20. The method of claim 12, wherein the alpha-1,3-glucan has at least about 90% alpha-1,3 glycosidic linkages.

* * * * *

SEQUENCE LISTING

<160> NUMBER OF SEQ ID NOS: 6

<210> SEQ ID NO 1
<211> LENGTH: 2319
<212> TYPE: DNA
<213> ORGANISM: Paenibacillus sp. N027

<400> SEQUENCE: 1

```
atgccgaaaa tcgcggacaa atatttacag gtcgacccct ggaaggtcgt ggaggtaggt      60
tttgatccgg ggcgtaaccg ggtcagcgag tcgattttt cactggggaa tgaatatatg     120
ggggtcagag gctacccgga ggaagggtat agcggagata cgctgctggg cagctatttc     180
aatgggctgt ttgaggagag cccggtgacg gctcattaca aggggattat taaatcgctg     240
cgctttatgg tgaacgcggt ggattggctt catacgcgga ttacattgga tggggaaacg     300
ctggatctgg cggtgagccg gttcagcaac tttcggcggg agctggattt tcgcacagga     360
atctataccc gggagttcgt gtggcatacc gccagcggga agacgtcca gattacgttt       420 gaacgcctcg tcagtatgaa ggtgtcccat cttggggcac agcggatgac gttgacgccg     480
ctcaacttca ctggttcgat tcaagtgcaa accggcctga acctgaaggt gatccatgag     540
gatcagcaac ggtgttattg gaaggagctg aaacagggg aagcaaaaga tatcgaagga     600
accgggatcg cggggattct aggggagacg gtgaacacgg ggaaccggtt gttttccgga     660
ttccgcgtag ttgcaccgga cgccgttacg gacgagttag tgcaggaaag ctgttacatc     720
ggccgggcgc tgaccttgaa gctggaacag ggcaagcgca gcacgctgga taaactcgtt     780
gtgaacgtgg ctgagaaaga ccgtaccacg ccggacgatg accttggct gcgagggatc       840 gagctgacag ctcggcacac ccaggcgggg tttgatgcgg cggcggccga ccaacgggcg     900
tattggaacc aggtgtgggc ggaatcggac atcgcgatcg aaggcgatcc ggagaatcag     960
caggggatcc gcttttgtat ttttcaactg tatcagactt accacgggga taaccccggc    1020
tttaacatcg gtgcaaaggg gctgaccggc gaggcttatc gggggctggc tttctgggat    1080
acggagtcgt attgcttgcc gttttatatt tttaacaatc gaaggcagc gcggagcttg       1140 ctcgaattcc gttatcggac gcttcctgag gcgttgaagc gggccaagga gctggactgt    1200
gaaggagcgt tttatccgat tgctaccatc gacggaacgg aaagctgcga tctgtggcag    1260
cactccaatc tgcagctgca tgtcggcacg gcggtagcgt acgggttgcg ccattatgtg    1320
aaaattacgg gtgacaaggc gtttctgtac gaaaaaggcg cggaaatgct gatccaaatc    1380
agccgttttt acgcgtcacg cggccagtgg gggcaacagt cgggcaaata cggctatttc    1440
ggcgtcatgg gcccggatga attccagctg atggtgaaca caactgtta tatcaacctg      1500 atggccaaga agttgttcga atatacgctg gaggtgctgg aagcgatgcg gagcgaggct    1560
ttcgccgctt atgacgagct ggcagcacgg cttggcctga cggaggaaga gcagaaggat    1620
tggcagaaca aggcgcagca tatgaaaatt ccgcgggatg aacggacggg gattttgaa      1680 gagcatgatg gcttttttga cctgccgcat ctggatattc acaccattcc ggtcacggag    1740
ttcccgctgt attcgcattg gtcgtatgat cgactctacc gttacgacat gattaagcag    1800
ccggatgtgc tgatgttcat gttcctgtac agcagcgaat actcgctcga ggaaaaacgc    1860
gctaactacg attattacga gccccgctgc attcacgaat cgtcgctgtc gccgtcgatc    1920
```

-continued

```
cactcgattt tggcggcgga atcggacgt tcggatgagg cgtataagtt ctttgaattt    1980
gcgacccggt tagacctgga caactataac cgcaatacgc gggaaggctt gcataccacg    2040
tcaattgcgg cagcttggat gaacattgtg tacgggttcg gcgggatgcg gtccgatggg    2100
gagttgcttg cgctgaatcc aagtatccct gaacggtggg aaagttaccg gtttatggtg    2160
acgtatcgcg gcacgaaact gcaagttgaa gtggaccaga atcaggttag catccgtgcg    2220
gtgtccggcg gcgtggcgga aattttggtg tatggcaacc tggtcaacat cgatgaagcc    2280
gggattcggt tgccgctccg aaaggcggtc gttcaatga                          2319
```

<210> SEQ ID NO 2
<211> LENGTH: 772
<212> TYPE: PRT
<213> ORGANISM: Paenibacillus sp. N027

<400> SEQUENCE: 2

```
Met Pro Lys Ile Ala Asp Lys Tyr Leu Gln Val Asp Pro Trp Lys Val
  1               5                  10                  15

Val Glu Val Gly Phe Asp Pro Gly Arg Asn Arg Val Ser Glu Ser Ile
                 20                  25                  30

Phe Ser Leu Gly Asn Glu Tyr Met Gly Val Arg Gly Tyr Pro Glu Glu
             35                  40                  45

Gly Tyr Ser Gly Asp Thr Leu Leu Gly Ser Tyr Phe Asn Gly Leu Phe
         50                  55                  60

Glu Glu Ser Pro Val Thr Ala His Tyr Lys Gly Ile Ile Lys Ser Leu
 65                  70                  75                  80

Arg Phe Met Val Asn Ala Val Asp Trp Leu His Thr Arg Ile Thr Leu
                 85                  90                  95

Asp Gly Glu Thr Leu Asp Leu Ala Val Ser Arg Phe Ser Asn Phe Arg
            100                 105                 110

Arg Glu Leu Asp Phe Arg Thr Gly Ile Tyr Thr Arg Glu Phe Val Trp
        115                 120                 125

His Thr Ala Ser Gly Lys Asp Val Gln Ile Thr Phe Glu Arg Leu Val
    130                 135                 140

Ser Met Lys Val Ser His Leu Gly Ala Gln Arg Met Thr Leu Thr Pro
145                 150                 155                 160

Leu Asn Phe Thr Gly Ser Ile Gln Val Gln Thr Gly Leu Asn Leu Lys
                165                 170                 175

Val Ile His Glu Asp Gln Gln Arg Cys Tyr Trp Lys Glu Leu Lys Gln
            180                 185                 190

Gly Glu Ala Lys Asp Ile Glu Gly Thr Gly Ile Ala Gly Ile Leu Gly
        195                 200                 205

Glu Thr Val Asn Thr Gly Asn Arg Leu Phe Ser Gly Phe Arg Val Val
    210                 215                 220

Ala Pro Asp Ala Val Thr Asp Glu Leu Val Gln Glu Ser Cys Tyr Ile
225                 230                 235                 240

Gly Arg Ala Leu Thr Leu Lys Leu Glu Gln Gly Lys Arg Ser Thr Leu
                245                 250                 255

Asp Lys Leu Val Val Asn Val Ala Glu Lys Asp Arg Thr Thr Pro Asp
            260                 265                 270

Asp Asp Leu Trp Leu Arg Gly Ile Glu Leu Thr Ala Arg His Thr Gln
        275                 280                 285

Ala Gly Phe Asp Ala Ala Ala Asp Gln Arg Ala Tyr Trp Asn Gln
    290                 295                 300
```

```
Val Trp Ala Glu Ser Asp Ile Ala Ile Glu Gly Asp Pro Glu Asn Gln
305                 310                 315                 320

Gln Gly Ile Arg Phe Cys Ile Phe Gln Leu Tyr Gln Thr Tyr His Gly
            325                 330                 335

Asp Asn Pro Gly Phe Asn Ile Gly Ala Lys Gly Leu Thr Gly Glu Ala
            340                 345                 350

Tyr Arg Gly Leu Ala Phe Trp Asp Thr Glu Ser Tyr Cys Leu Pro Phe
            355                 360                 365

Tyr Ile Phe Asn Asn Pro Lys Ala Ala Arg Ser Leu Leu Glu Phe Arg
370                 375                 380

Tyr Arg Thr Leu Pro Glu Ala Leu Lys Arg Ala Lys Glu Leu Asp Cys
385                 390                 395                 400

Glu Gly Ala Phe Tyr Pro Ile Ala Thr Ile Asp Gly Thr Glu Ser Cys
            405                 410                 415

Asp Leu Trp Gln His Ser Asn Leu Gln Leu His Val Gly Thr Ala Val
            420                 425                 430

Ala Tyr Gly Leu Arg His Tyr Val Lys Ile Thr Gly Asp Lys Ala Phe
            435                 440                 445

Leu Tyr Glu Lys Gly Ala Glu Met Leu Ile Gln Ile Ser Arg Phe Tyr
450                 455                 460

Ala Ser Arg Gly Gln Trp Gly Gln Gln Ser Gly Lys Tyr Gly Tyr Phe
465                 470                 475                 480

Gly Val Met Gly Pro Asp Glu Phe Gln Leu Met Val Asn Asn Asn Cys
            485                 490                 495

Tyr Ile Asn Leu Met Ala Lys Lys Leu Phe Glu Tyr Thr Leu Glu Val
            500                 505                 510

Leu Glu Ala Met Arg Ser Glu Ala Phe Ala Ala Tyr Asp Glu Leu Ala
            515                 520                 525

Ala Arg Leu Gly Leu Thr Glu Glu Gln Lys Asp Trp Gln Asn Lys
530                 535                 540

Ala Gln His Met Lys Ile Pro Arg Asp Glu Arg Thr Gly Ile Phe Glu
545                 550                 555                 560

Glu His Asp Gly Phe Phe Asp Leu Pro His Leu Asp Ile His Thr Ile
            565                 570                 575

Pro Val Thr Glu Phe Pro Leu Tyr Ser His Trp Ser Tyr Asp Arg Leu
            580                 585                 590

Tyr Arg Tyr Asp Met Ile Lys Gln Pro Asp Val Leu Met Phe Met Phe
            595                 600                 605

Leu Tyr Ser Ser Glu Tyr Ser Leu Glu Glu Lys Arg Ala Asn Tyr Asp
            610                 615                 620

Tyr Tyr Glu Pro Arg Cys Ile His Glu Ser Ser Leu Ser Pro Ser Ile
625                 630                 635                 640

His Ser Ile Leu Ala Ala Glu Ile Gly Arg Ser Asp Glu Ala Tyr Lys
            645                 650                 655

Phe Phe Glu Phe Ala Thr Arg Leu Asp Leu Asp Asn Tyr Asn Arg Asn
            660                 665                 670

Thr Arg Glu Gly Leu His Thr Thr Ser Ile Ala Ala Ala Trp Met Asn
            675                 680                 685

Ile Val Tyr Gly Phe Gly Gly Met Arg Ser Asp Gly Glu Leu Leu Ala
            690                 695                 700

Leu Asn Pro Ser Ile Pro Glu Arg Trp Glu Ser Tyr Arg Phe Met Val
705                 710                 715                 720

Thr Tyr Arg Gly Thr Lys Leu Gln Val Glu Val Asp Gln Asn Gln Val
```

725                 730                 735
Ser Ile Arg Ala Val Ser Gly Gly Val Ala Glu Ile Leu Val Tyr Gly
            740                 745                 750

Asn Leu Val Asn Ile Asp Glu Ala Gly Ile Arg Leu Pro Leu Arg Lys
        755                 760                 765

Ala Val Val Gln
    770

<210> SEQ ID NO 3
<211> LENGTH: 2319
<212> TYPE: DNA
<213> ORGANISM: Artificial sequence
<220> FEATURE:
<223> OTHER INFORMATION: Codon-optimized sequence encoding PspGp3

<400> SEQUENCE: 3

```
gtgcctaaaa ttgcggataa atatcttcaa gtcgatccgt ggaaagtggt cgaagtcggc        60
tttgatccgg ccgtaatag agtgagcgaa tctatcttta gcctgggcaa cgaatatatg       120
ggagttcgtg gctatcctga agaaggctat agcggcgata cattactggg ctcttatttt       180
aacggtctgt tgaagaaag cccggtgaca gctcattaca agggcatcat caaatcactt       240
cggtttatgg tcaatgcagt ggattggtta catacacgca ttacgctgga tggcgaaaca       300
cttgatcttg cagtctctcg gtttagcaat tttcgccgcg aacttgattt tcgtacgggc       360
atctatacga gagaatttgt gtggcatacg gcgtcaggca agatgtcca gattacgttt       420
gaacgccttg tctctatgaa agtgagccat ctcggagcac aacgcatgac actgacaccg       480
ttaaatttta cgggctctat tcaggtccag acgggcctta tcttaaagt catccatgaa       540
gatcaacaac gttgttattg aaagaactt aaacagggtg aagctaaaga cattgaaggc       600
acgggaattg caggcatcct gggagaaacg gtcaatacag caatagact gtttagcggc       660
tttcgtgtgg tcgcaccgga tgctgtcaca gatgaattag tccaggaatc atgctatatc       720
ggtcgtgctc tgacgcttaa actggaacaa ggcaaacgta gcacgttaga taaactggtc       780
gtcaatgtcg cggaaaaaga tcgcacgaca cctgatgatg atctgtggtt gagaggcatc       840
gaactgacag ctcgccatac acaagcgggc tttgatgcag ctgctgcgga tcagcgtgcg       900
tattggaatc aggtgtgggc ggaatcagat attgcgatcg aaggcgatcc ggaaaatcag       960
cagggcatcc gcttttgcat ctttcagttg tatcagacat atcatggcga taatccgggc      1020
ttaatatcg cgctaaagg actgacggga gaagcgtata gaggacttgc attttgggat      1080
acagaaagct attgccttcc gttttatatc tttaataacc gaaagctgc gcgcagctta      1140
ctggaatttc ggtatcgtac cttaccggaa gcacttaaac gtgctaaaga actggattgt      1200
gaaggcgcgt tttatccgat gcgacgatc gatggcacga atcatgcga tttgtggcaa      1260
cattctaatc ttcagttaca tgtcggcaca gcagtcgcgt atggccttcg ccattatgtc      1320
aaaatcacgg gagataaagc gtttctgtat gaaaaaggcg ctgaaatgtt gatccaaatc      1380
tcacgcttt atgcgagccg cggacaatgg gggcagcaga gcggcaaata tggctatttt      1440
ggagtcatgg gaccggatga atttcaactt atggtcaaca caattgtta tattaatctg      1500
atggctaaaa aactgtttga atatacgtta gaagttctgg aagcaatgcg tagcgaagcg      1560
tttgctgcgt atgatgaact tgctgctcgt ctgggactga cggaagaaga acaaaaagat      1620
tggcaaaaca aggcacaaca catgaaaatt cctagagatg aacgcacagg catctttgaa      1680
gaacatgatg gctttttcga tctgcctcat ctggatattc atacgattcc tgtgacagaa      1740
```

| | |
|---|---|
| tttcctctgt attcacattg gtcttacgat cggttgtata gatatgatat gatcaaacaa | 1800 |
| ccggatgtgt taatgtttat gtttctgtat agctcagaat attctctgga agaaaaacgt | 1860 |
| gctaattatg attattatga acctcggtgc atccatgaat ctagcctgag cccgagcatc | 1920 |
| cattctatct tagctgcgga aataggccgt tctgatgaag cgtataagtt ctttgaattt | 1980 |
| gctacacgcc ttgatttgga taattataat cgcaatacac gcgaaggact tcatacgacg | 2040 |
| tctattgcag cagcttggat gaatatcgtc tatggctttg gaggaatgcg ctcagatggc | 2100 |
| gaacttcttg cacttaatcc tagcattccg gaacggtggg aaagctatcg gtttatggtg | 2160 |
| acgtatagag gaacgaaact tcaagtcgaa gtcgatcaaa tcaggtgtc tattcgcgca | 2220 |
| gtgagcggcg gtgttgcaga atccttgtg tatggcaacc tcgttaatat cgatgaagcg | 2280 |
| ggcattcgcc tgccgctgcg caaagcagtt gtccaataa | 2319 |

<210> SEQ ID NO 4
<211> LENGTH: 2298
<212> TYPE: DNA
<213> ORGANISM: Caldicellulosiruptor hydrothermalis

<400> SEQUENCE: 4

| | |
|---|---|
| gtgataaata aaagggtag cagatatgta aagtagatc catggtgcat catagaagaa | 60 |
| aattttgaca aatcaaacat gagggtttta gaatctctgt ttactgtgag taacggttac | 120 |
| attggtacaa gaggctactt tgatgagttt tacacagggg atactcacat cggcacttac | 180 |
| gttgcaggtg tgtttgaaga aatatatgaa aaaccttcgt acaaaggagt gccaaacaga | 240 |
| acccagtttg ttgtcaacaa tgcaaactgg ctgtacacaa gaattattgc agatggtgag | 300 |
| gagcttgacc tgaaccattc taattttttcg gagtacaaaa gagtgcttga tcttaaaaaa | 360 |
| ggtattttga caagagaatt tatttggcac accgaaaaag ggtcaagttt taagctcaag | 420 |
| tttgaaagat ttattagcat gactaaaagc aatgtatgct gtcagaagat agaaatcaca | 480 |
| tcgttgaata aagtggtaa ggtaaaaaatc atcagtgggg ttgattttttc tcacaagcac | 540 |
| aggatatatg acacaaacta ctgggagggc ttatttaaat caaatgaaaa tgattacatc | 600 |
| tctattggat gtaaaacaat aaagaccaac aaaataagca ttgcaaactt taaaatagag | 660 |
| gcaaacaagg catgtgagca aggaattgtt gaaggagaga agatcatagc aaaagagatg | 720 |
| gtttttgata tagaagaaaa tgaaaccata gagattgaaa aggttgttgt tataaattcg | 780 |
| tttgatagat taaatgaaaa tttgcagagc aaaaatggaa agctttgtca gtccgtatt | 840 |
| ggtcaatata gctattcaaa gctgaaacaa gagcacgaaa gattctggga gaggatgtgg | 900 |
| gaagaagttg atattgaaat agggcaagat agcgaaaatc agcagggtat aaggttctgc | 960 |
| atattccaga tgctgcaagc atactcaggc atgcaacagg ttgttgctgg gattggtgca | 1020 |
| aaaggtttaa gcggtgaagt atacaatggc aattcgttct gggacagtga agtttactgt | 1080 |
| cttccattct acctatttac aaacattgat gcagcaaaaa gcttttaga gtttagatac | 1140 |
| tatacccctgc cccaggcaca acaaagagct aaagagcttg atttgaaagg agcattttat | 1200 |
| ccaatcgcca caattgatgg cacagagtca tgtacgctgt ggcagcatgc gaatttgcag | 1260 |
| cttcaggtaa gtcagccgt tgcatatgga ctttatcact attatattgt cacaaaagat | 1320 |
| gaaaagtttt tgtttgaaaa agggacagag atattaattg aagtttgtag gatgctggag | 1380 |
| agtaggtgtc aacttgggca aaaagatggc aagtatggct ttttttggagt aatgggacct | 1440 |
| gatgagtttc acatgatggt aaacaacgat ttttacacaa attacatggc aaaaaagagt | 1500 |
| ttagagttta caatagaggt cttgaaacta ctaaaagcca aagatgaaaa attatataat | 1560 |

-continued

```
gaaataacca gaaaaacaaa acttgaaaga aatgaagttg aaagatgggc tgatattgca      1620
aaaaatatga aaataattca agaccctcag agcaaggtgt tgaacagca  tgaaggctat      1680 tttaacctgc ctcatattga actttcaaca attcccgaag accaaattcc aatatacaaa      1740
aattgggcct atgacaggat attcaggtat gacatgataa aacagcctgc agttttgctc      1800
tgcatgcttc tttatagctg tgactttttct tttgaagaga aaaaagcaaa ttatgactat      1860
tatgatttga ggtgtattca tgaatcgtca ctgtctcctt caattcattc tattctggca      1920
tgtgaacttg gctattatga caaggcttat gagtacttca ggtatgccac acgcctggac      1980
cttgacaatt acaacagaaa cactgaagaa ggacttcata taacctcgct ggctgcggca      2040
tggctgaaca tcgtctacgg ttttggtggt atgagatctg atacagcgcc cataaagctt      2100
gctccaatca ttccagataa ctggagttat tattctttca gaatcaaata taatggagcg      2160
gtattaaaga tagttgtaga cccacagtat gttactatca aaaagctcaa aggtgcagat      2220
gttgagctga tggtttatga taaaacctac accataacag aagatgagat taaaatcccg      2280
cttcagaaaa ggaggtaa                                                    2298
```

<210> SEQ ID NO 5
<211> LENGTH: 765
<212> TYPE: PRT
<213> ORGANISM: Caldicellulosiruptor hydrothermalis

<400> SEQUENCE: 5

```
Met Ile Asn Lys Lys Gly Ser Arg Tyr Val Lys Val Asp Pro Trp Cys
1               5                   10                  15

Ile Ile Glu Glu Asn Phe Asp Lys Ser Asn Met Arg Val Leu Glu Ser
            20                  25                  30

Leu Phe Thr Val Ser Asn Gly Tyr Ile Gly Thr Arg Gly Tyr Phe Asp
        35                  40                  45

Glu Phe Tyr Thr Gly Asp Thr His Ile Gly Thr Tyr Val Ala Gly Val
    50                  55                  60

Phe Glu Glu Ile Tyr Glu Lys Pro Ser Tyr Lys Gly Val Pro Asn Arg
65                  70                  75                  80

Thr Gln Phe Val Val Asn Asn Ala Asn Trp Leu Tyr Thr Arg Ile Ile
                85                  90                  95

Ala Asp Gly Glu Glu Leu Asp Leu Asn His Ser Asn Phe Ser Glu Tyr
            100                 105                 110

Lys Arg Val Leu Asp Leu Lys Lys Gly Ile Leu Thr Arg Glu Phe Ile
        115                 120                 125

Trp His Thr Glu Lys Gly Ser Ser Phe Lys Leu Lys Phe Glu Arg Phe
    130                 135                 140

Ile Ser Met Thr Lys Ser Asn Val Cys Cys Gln Lys Ile Glu Ile Thr
145                 150                 155                 160

Ser Leu Asn Lys Ser Gly Lys Val Lys Ile Ser Gly Val Asp Phe
                165                 170                 175

Ser His Lys His Arg Ile Tyr Asp Thr Asn Tyr Trp Glu Gly Leu Phe
            180                 185                 190

Lys Ser Asn Glu Asn Asp Tyr Ile Ser Ile Gly Cys Lys Thr Ile Lys
        195                 200                 205

Thr Asn Lys Ile Ser Ile Ala Asn Phe Lys Ile Glu Ala Asn Lys Ala
    210                 215                 220

Cys Glu Gln Gly Ile Val Glu Gly Glu Lys Ile Ile Ala Lys Glu Met
225                 230                 235                 240
```

```
Val Phe Asp Ile Glu Glu Asn Glu Thr Ile Glu Ile Glu Lys Val Val
                245                 250                 255

Val Ile Asn Ser Phe Asp Arg Leu Asn Glu Asn Leu Gln Ser Lys Asn
                260                 265                 270

Gly Lys Leu Cys Gln Ser Val Phe Gly Gln Tyr Ser Tyr Ser Lys Leu
                275                 280                 285

Lys Gln Glu His Glu Arg Phe Trp Glu Arg Met Trp Glu Glu Val Asp
            290                 295                 300

Ile Glu Ile Gly Gln Asp Ser Glu Asn Gln Gln Gly Ile Arg Phe Cys
305                 310                 315                 320

Ile Phe Gln Met Leu Gln Ala Tyr Ser Gly Met Gln Gln Val Val Ala
                325                 330                 335

Gly Ile Gly Ala Lys Gly Leu Ser Gly Glu Val Tyr Asn Gly Asn Ser
                340                 345                 350

Phe Trp Asp Ser Glu Val Tyr Cys Leu Pro Phe Tyr Leu Phe Thr Asn
                355                 360                 365

Ile Asp Ala Ala Lys Lys Leu Leu Glu Phe Arg Tyr Tyr Thr Leu Pro
                370                 375                 380

Gln Ala Gln Gln Arg Ala Lys Glu Leu Asp Leu Lys Gly Ala Phe Tyr
385                 390                 395                 400

Pro Ile Ala Thr Ile Asp Gly Thr Glu Ser Cys Thr Leu Trp Gln His
                405                 410                 415

Ala Asn Leu Gln Leu Gln Val Ser Thr Ala Val Ala Tyr Gly Leu Tyr
                420                 425                 430

His Tyr Tyr Ile Val Thr Lys Asp Glu Lys Phe Leu Phe Glu Lys Gly
                435                 440                 445

Thr Glu Ile Leu Ile Glu Val Cys Arg Met Leu Glu Ser Arg Cys Gln
450                 455                 460

Leu Gly Gln Lys Asp Gly Lys Tyr Gly Phe Phe Gly Val Met Gly Pro
465                 470                 475                 480

Asp Glu Phe His Met Met Val Asn Asn Asp Phe Tyr Thr Asn Tyr Met
                485                 490                 495

Ala Lys Lys Ser Leu Glu Phe Thr Ile Glu Val Leu Lys Leu Leu Lys
                500                 505                 510

Ala Lys Asp Glu Lys Leu Tyr Asn Glu Ile Thr Arg Lys Thr Lys Leu
                515                 520                 525

Glu Arg Asn Glu Val Glu Arg Trp Ala Asp Ile Ala Lys Asn Met Lys
                530                 535                 540

Ile Ile Gln Asp Pro Gln Ser Lys Val Phe Glu Gln His Glu Gly Tyr
545                 550                 555                 560

Phe Asn Leu Pro His Ile Glu Leu Ser Thr Ile Pro Glu Asp Gln Ile
                565                 570                 575

Pro Ile Tyr Lys Asn Trp Ala Tyr Asp Arg Ile Phe Arg Tyr Asp Met
                580                 585                 590

Ile Lys Gln Pro Ala Val Leu Leu Cys Met Leu Leu Tyr Ser Cys Asp
                595                 600                 605

Phe Ser Phe Glu Glu Lys Lys Ala Asn Tyr Asp Tyr Tyr Asp Leu Arg
                610                 615                 620

Cys Ile His Glu Ser Ser Leu Ser Pro Ser Ile His Ser Ile Leu Ala
625                 630                 635                 640

Cys Glu Leu Gly Tyr Tyr Asp Lys Ala Tyr Glu Tyr Phe Arg Tyr Ala
                645                 650                 655
```

```
Thr Arg Leu Asp Leu Asp Asn Tyr Asn Arg Asn Thr Glu Glu Gly Leu
            660                 665                 670

His Ile Thr Ser Leu Ala Ala Ala Trp Leu Asn Ile Val Tyr Gly Phe
            675                 680                 685

Gly Gly Met Arg Ser Asp Thr Ala Pro Ile Lys Leu Ala Pro Ile Ile
            690                 695                 700

Pro Asp Asn Trp Ser Tyr Tyr Ser Phe Arg Ile Lys Tyr Asn Gly Ala
705                 710                 715                 720

Val Leu Lys Ile Val Asp Pro Gln Tyr Val Thr Ile Lys Lys Leu
                725                 730                 735

Lys Gly Ala Asp Val Glu Leu Met Val Tyr Asp Lys Thr Tyr Thr Ile
            740                 745                 750

Thr Glu Asp Glu Ile Lys Ile Pro Leu Gln Lys Arg Arg
            755                 760                 765

<210> SEQ ID NO 6
<211> LENGTH: 2298
<212> TYPE: DNA
<213> ORGANISM: Artificial sequence
<220> FEATURE:
<223> OTHER INFORMATION: Codon-optimized sequence encoding ChyGp1

<400> SEQUENCE: 6
gtgattaata agaaaggctc tcgttatgtc aaagttgatc cgtggtgcat catcgaagaa      60
aattttgata atctaatat gcgggtgtta gagtccttgt ttacagtgag caatggctat     120
atcggcacgc ggggctattt tgatgaattt tatacgggag atacacatat cgggacttat     180
gtcgcgggag tgtttgaaga aatctatgaa aaaccgagct ataagggcgt ccctaatcgc     240
acacagtttg tcgtcaataa cgcgaattgg ctgtatacac gcatcattgc agatggagaa     300
gaactggatc tgaatcatag caattttagc gaatataagc gggtcctgga tcttaaaaaa     360
ggcattctga cgagagagtt catctggcat acggaaaaag ctctagcttt aaacttaaaa     420
tttgaacgct ttattagcat gacgaaatct aatgtctgct gccagaaaat cgaaattaca     480
agccttaaca atcaggcaa agtcaaaatc atctctggag tcgattttag ccataaacat     540
cgcatctatg atacgaatta ttgggaagga ctgtttaaat ctaacgagaa tgattatatc     600
tctatcggct gcaaaacaat caaaacgaac aaaatctcta ttgctaattt taaaattgaa     660
gctaacaaag cgtgtgaaca gggcattgtg agggagaaa aaatcattgc taaagaaatg     720
gtctttgata tagaagaaaa cgaaacgatt gaaatcgaaa agttgtcgt catcaatagc     780 tttgatagac ttaacgaaaa tcttcagagc aaaaatggca aactgtgcca gtcagtgttt     840
ggacagtatt catatagcaa acttaaacag gaacatgaac ggttttggga acgcatgtgg     900
gaagaagtgg atattgaaat cggccaggat agcgaaaatc agcagggcat tcggttttgt     960 atcttcaga tgttacaagc gtattcaggg atgcagcagg tggtcgcggg catcggcgct    1020
aaaggcctga cggcgaagt ctataatgcc aatagctttt gggattcaga agtctattgc    1080
cttccgtttt atctgtttac gaatatcgat gcagctaaaa aactgctgga atttcggtat    1140
tatacacttc ctcaagcaca acaacgtgct aaagaactgg atcttaaagg cgcgttttat    1200
ccgattgcga caatcgatgg cacggaatct tgtacgctgt ggcaacatgc gaatcttcag    1260
ttacaggtct ctacagcggt cgcgtatggc ctgtatcatt attatatcgt gacgaaagat    1320
gaaaaatttc tgttttgaaaa aggcacagaa attctgattg aagtgtgccg gatgctggaa    1380
agccggtgcc agttaggaca gaaagatggc aaatatggct ctttggagt catgggaccg    1440
```

```
                                                                                  -continued gatgaatttc acatgatggt caataacgat ttttatacga attatatggc taaaaaatca  1500
ctggagttca cgatcgaagt ccttaaactt cttaaagcta aagatgaaaa actgtataat  1560
gagatcacaa gaaaaacgaa actggaacgc aacgaagtgg aacgttgggc ggacattgct  1620
aaaaatatga aaatcatcca agatcctcag agcaaagtgt ttgaacaaca tgaaggctat  1680
tttaatctac ctcatatcga actttctacg atcccggaag atcagattcc gatctacaaa  1740
aattgggcgt atgatcgcat ctttcggtat gatatgatca aacaacctgc tgtcctgctg  1800
tgcatgttac tgtattcttg cgattttagc tttgaagaaa agaaggctaa ttatgattat  1860
tatgatcttc gttgcatcca tgaatcaagc ctgagcccta gcatccattc tatccttgcg  1920
tgcgaactgg gctattatga taaagcgtat gaatattttc ggtatgcgac gcggttagac  1980
ctagataatt ataatcgtaa tacggaagaa ggacttcata tcacgtcact tgcagcggcg  2040
tggcttaata ttgtgtatgg ctttggagga atgcgctcag atacagcgcc gatcaaactt  2100
gctccgatta tcccggataa ttggtcttat tatagctttc gcatcaaata taatggcgca  2160
gtccttaaaa ttgtcgtcga tcctcagtat gtgacgatca aaaaacttaa aggcgctgat  2220
gtggaactga tggtgtatga taaaacgtat acgatcacgg aagatgaaat caaaattccg  2280
ttgcagaaac gccgctaa                                                2298
```